United States Patent
Barsoum et al.

(10) Patent No.: US 7,256,181 B2
(45) Date of Patent: *Aug. 14, 2007

(54) METHODS AND COMPOSITIONS FOR THERAPIES USING GENES ENCODING SECRETED PROTEINS SUCH AS INTERFERON-BETA

(75) Inventors: James G Barsoum, Lexington, MA (US); Albert X Qin, Winchester, MA (US)

(73) Assignee: Biogen Idec MA Inc., Cambridge, MA (US)

(*) Notice: Subject to any disclaimer, the term of this patent is extended or adjusted under 35 U.S.C. 154(b) by 7 days.

This patent is subject to a terminal disclaimer.

(21) Appl. No.: 10/395,712

(22) Filed: Mar. 20, 2003

(65) Prior Publication Data

US 2003/0229042 A1    Dec. 11, 2003

Related U.S. Application Data

(63) Continuation of application No. 09/512,946, filed on Feb. 25, 2000, now Pat. No. 6,696,423, which is a continuation of application No. PCT/US98/17606, filed on Aug. 25, 1998.

(60) Provisional application No. 60/057,254, filed on Aug. 29, 1997.

(51) Int. Cl.
*A61K 48/00* (2006.01)
*C12N 15/63* (2006.01)
*C12N 15/87* (2006.01)

(52) U.S. Cl. ............. 514/44; 435/320.1; 435/455; 435/325

(58) Field of Classification Search .......... 514/44; 435/320.1, 325, 455
See application file for complete search history.

(56) References Cited

U.S. PATENT DOCUMENTS

| | | | |
|---|---|---|---|
| 4,980,286 A | 12/1990 | Morgan et al. | |
| 5,240,846 A | 8/1993 | Collins et al. | |
| 5,518,913 A | 5/1996 | Massie et al. | |
| 5,543,328 A | 8/1996 | McClelland et al. | |
| 5,552,309 A | 9/1996 | March | |
| 5,585,237 A | 12/1996 | Oppermann et al. | |
| 5,585,362 A | 12/1996 | Wilson et al. | |
| 5,631,236 A | 5/1997 | Woo et al. | |
| 5,662,896 A | 9/1997 | Barber et al. | |
| 5,670,488 A | 9/1997 | Gregory et al. | |
| 5,677,178 A | 10/1997 | McCormick | |
| 5,698,531 A | 12/1997 | Nabel et al. | |
| 5,700,470 A | 12/1997 | Saito et al. | |
| 5,707,618 A | 1/1998 | Armentano et al. | |
| 5,707,969 A | 1/1998 | Nabel et al. | |
| 5,801,029 A | 9/1998 | McCormick | |
| 5,824,544 A | 10/1998 | Armentano et al. | |
| 5,830,880 A | 11/1998 | Sedlacek et al. | |
| 5,831,062 A | 11/1998 | Taylor et al. | |
| 5,837,511 A | 11/1998 | Falck-Pedersen et al. | |
| 5,846,945 A | 12/1998 | McCormick | |
| 5,849,561 A | 12/1998 | Falck-Pedersen | |
| 5,851,806 A | 12/1998 | Kovesdi et al. | |
| 5,856,181 A | 1/1999 | McCormick | |
| 5,866,552 A | 2/1999 | Wilson et al. | |
| 5,876,974 A | 3/1999 | Gregory | |
| 5,880,102 A | 3/1999 | George et al. | |
| 5,882,877 A | 3/1999 | Gregory et al. | |
| 5,932,210 A | 8/1999 | Gregory et al. | |
| 5,935,935 A | 8/1999 | Connelly et al. | |
| 5,952,221 A | 9/1999 | Kurtzman et al. | |
| 5,972,706 A | 10/1999 | McCormick | |
| 5,981,225 A | 11/1999 | Kochanek et al. | |
| 5,981,274 A | 11/1999 | Tyrrell et al. | |
| 5,994,106 A | 11/1999 | Kovesdi et al. | |
| 5,994,128 A | 11/1999 | Fallaux et al. | |
| 5,997,859 A | 12/1999 | Barber et al. | |
| 6,001,557 A | 12/1999 | Wilson et al. | |
| 6,013,638 A | 1/2000 | Crystal et al. | |
| 6,020,191 A | 2/2000 | Scaria et al. | |
| 6,033,885 A | 3/2000 | Latta et al. | |
| 6,033,908 A | 3/2000 | Bout et al. | |
| 6,040,174 A | 3/2000 | Imler et al. | |
| 6,057,158 A | 5/2000 | Chamberlain et al. | |
| 6,063,622 A | 5/2000 | Chamberlain et al. | |
| 6,066,624 A * | 5/2000 | Woo et al. ............. | 514/44 |

(Continued)

FOREIGN PATENT DOCUMENTS

AU    B-37570/93    10/1993

(Continued)

OTHER PUBLICATIONS

Gorzilglia et al. (1996) J. Virol., vol. 70 (6), 4173-4178.*

(Continued)

*Primary Examiner*—Anne M. Wehbe
(74) *Attorney, Agent, or Firm*—Sterne, Kessler, Goldstein & Fox, P.L.L.C.

(57) ABSTRACT

Methods and pharmaceutical compositions for modifying cells of a mammalian recipient with DNA encoding a secreted protein such as human interferon in situ are provided. The methods include forming a secreted protein expression system in vivo or ex vivo and administering the expression system to the mammalian recipient. The expression system and methods are useful for the localized and systemic delivery of interferons in situ.

31 Claims, 5 Drawing Sheets

U.S. PATENT DOCUMENTS

| | | | |
|---|---|---|---|
| 6,080,569 A | 6/2000 | Graham et al. | |
| 6,083,750 A | 7/2000 | Chamberlain et al. | |
| 6,093,567 A | 7/2000 | Gregory et al. | |
| 6,100,086 A | 8/2000 | Kaplan et al. | |
| 6,120,764 A | 9/2000 | Graham et al. | |
| 6,136,594 A | 10/2000 | Dalemans et al. | |
| 6,140,087 A | 10/2000 | Graham et al. | |
| 6,140,103 A | 10/2000 | Einerhand et al. | |
| 6,203,975 B1 | 3/2001 | Wilson et al. | |
| 6,204,052 B1 | 3/2001 | Bout et al. | |
| 6,204,060 B1 | 3/2001 | Mehtali et al. | |
| 6,210,939 B1 | 4/2001 | Gregory et al. | |
| 6,218,180 B1 | 4/2001 | Kurtzman et al. | |
| 6,228,646 B1 | 5/2001 | Hardy | |
| 6,241,982 B1 | 6/2001 | Barber et al. | |
| 6,281,010 B1 | 8/2001 | Gao et al. | |
| 6,297,219 B1 | 10/2001 | Nabel et al. | |
| 6,303,362 B1 | 10/2001 | Kay et al. | |
| 6,312,681 B1 | 11/2001 | Engler et al. | |
| 6,312,946 B1 | 11/2001 | Yeh et al. | |
| 6,348,450 B1 | 2/2002 | Tang et al. | |
| 6,531,456 B1* | 3/2003 | Kurtzman et al. | 514/44 |
| 6,696,423 B1* | 2/2004 | Barsoum et al. | 514/44 |
| 2002/0006395 A1 | 1/2002 | Perricaudet et al. | |
| 2002/0034505 A1 | 3/2002 | Nabel et al. | |
| 2002/0197236 A1 | 12/2002 | Nabel et al. | |
| 2004/0086486 A1 | 5/2004 | Barsoum et al. | |
| 2004/0265288 A1 | 12/2004 | Gilman | |

FOREIGN PATENT DOCUMENTS

| | | |
|---|---|---|
| AU | B-61444/94 | 9/1994 |
| AU | B-65721/94 | 11/1994 |
| AU | 704919 | 6/1995 |
| AU | 716508 | 1/1997 |
| EP | 0 070 906 B1 | 10/1986 |
| EP | 0 707 071 A1 | 8/1995 |
| EP | 0 777 740 B1 | 6/1997 |
| EP | 0 804 601 B1 | 11/1997 |
| JP | 57-130998 A | 8/1982 |
| JP | 8506970 | 7/1996 |
| JP | 8-238092 A | 9/1996 |
| WO | WO 85/05125 | 11/1985 |
| WO | WO 88/00971 | 2/1988 |
| WO | WO 90/11734 | 10/1990 |
| WO | WO 93/00051 | 1/1993 |
| WO | WO 93/00052 | 1/1993 |
| WO | WO 93/19191 | 9/1993 |
| WO | WO 94/08026 | 4/1994 |
| WO | WO 94/11506 | 5/1994 |
| WO | WO 94/12649 | 6/1994 |
| WO | WO 94/18992 | 9/1994 |
| WO | WO 94/20146 | 9/1994 |
| WO | WO 94/24297 | 10/1994 |
| WO | WO 94/28152 | 12/1994 |
| WO | WO 94/28938 | 12/1994 |
| WO | WO 95/14785 | 6/1995 |
| WO | WO 95/16784 | 6/1995 |
| WO | WO 95/34671 | 12/1995 |
| WO | WO96/06939 | 3/1996 |
| WO | WO96/06940 | 3/1996 |
| WO | WO 96/12030 | 4/1996 |
| WO | WO 97/00947 | 1/1997 |
| WO | WO 97/20943 | 6/1997 |
| WO | WO 97/21826 | 6/1997 |
| WO | WO 97/32991 | 9/1997 |
| WO | WO 97/42323 | 11/1997 |
| WO | WO 98/39418 | 9/1998 |
| WO | WO 98/53087 | 11/1998 |
| WO | WO 99/41398 | 8/1999 |
| WO | WO 00/72679 | 12/2000 |

OTHER PUBLICATIONS

Verma et al. (1997) Nature, vol. 389, 239-242.*
Marshall et al. (1995) Science, vol. 269, 1050-1055.*
Orkin et al. (1995) "Report and Recommendation to the NIH", p. 1-23.*
Deonarian et al. (1998) Exp. Opin. Ther. Patents, vol. 9(1), 53-69.*
Miller et al. (1995) FASEB, vol. 9, 90-99.*
Lusky, M., "Good manufacturing practice production of adenoviral vectors for clinical trials" Human Gene Therapy 16: 281-291 (Mar. 2005).
Einhorn et al., "Why Do So Many Cancer Patients Fail to Respond to Interferon Therapy?" Journal of Interferon and Cytokine Research 16:275-281 (1996).
Johns et al., "Antiproliferative Potencies of Interferons on Melanoma Cell Lines and Xenografts: Higher Efficacy of Interferon β" Journal of the National Cancer Institute vol. 84, No. 15: 1185-1190 (Aug. 5, 1992).
Garbe et al., "Antitumor Activities of Interferon Alpha, Beta, and Gamma and Their Combinations on Human Melanoma Cells In Vitro: Changes of Proliferation, Melanin Synthesis, and Immunophenotype" The Journal of Investigative Dermatology vol. 95, No. 6, Supplement: 231S-237S (1990).
Arbaje et al., "Antiproliferative Effects of Interferons -α and -β in Combination with 5-Fluorouracil, Cisplatin, and Cis- and Trans-Retinoic Acid in Three Human Lung Carcinoma Cell lines" Journal of Interferon Research 13:25-32 (1993).
Rosenblum et al., "Growth Inhibitory Effects of Interferon-β But Not Interferon-α on Human Glioma Cells: Correlation of Receptor Binding, 2', 5' -Oligoadenylate Synthetase and Protein Kinase Activity" Journal of Interferon Research 10:141-151 (1990).
Hertzog et al., "Comparative Antiproliferative and Receptor Binding Activities of Interferons α and β on Lymphoblastoid and Melanoma Cells" Biochemistry International vol. 22, No. 6: 1095-1102 (1990).
Borden et al., "Second-generation Interferons For Cancer: Clinical Targets" seminars in Cancer Biology vol. 10: 125-144 (2000).
Hansen et al., "Current Status of Interferons In the Treatment of Cancer" Oncology, vol. 6, No. 11: 19-24 (1992).
Dorr, "Interferon-α in Malignant and Viral Diseases" Drugs 45 (2): 177-211 (1993).
Wadler et al., "Antineoplastic Activity of The Combination of Interferon and Cytotoxic Agents against Experimental and Human Malignancies: A Review" Cancer Research 50, 3473-3486, (1990).
Minakuchi et al., "Remarkable and Persistent Shrinkage of Uterine Leiomyoma Associated with Interferon alfa Treatment for Hepatitis" The Lancet vol. 353: 2127-2128 (1999).
Schiller et al., "Phase II Trial of a Combination of Interferon-βser and Interferon-γ in Patients with Advanced Malignant Melanoma" Journal of Interferon Research 8:581-589 (1988).
Ikic et al., "Treatment of Squamous Cell Carcinoma with Interferon" Pharmacology and Therapeutics vol. 30, No. 1: 58-61 (1991).
Kirkwood et al., "Role of Interferons in the Therapy of Melanoma" The Journal of Investigative Dermatology vol. 95, No. 6, Supplement: pp. 180S-184S (1990).
Vokes, "The Promise of Biochemical Modulation in Combined Modality Therapy" Seminars in Oncology vol. 21, No. 6, Suppl. 14: 29-33 (1994).
Porzsolt et al., "Rationale for Combining Tamoxifen and Interferon in the Treatment of Advanced Breast Cancer" Journal of Cancer Research and Clinical Oncology 115: 465-469 (1989).
McDonald et al., "Combined Betaseron R (Recombinant Human Interferon Beta) and Radiation for Inoperable Non-Small Cell Lung Cancer" Int. J. Radiation Oncology Biology Physics vol. 27, No. 3: 613-619 (1993).
Spiegel, "Additional Indications for Interferon Therapy: Basal Cell Carcinoma, Carcinoid, and Chronic Active Hepatitis" Seminars in Oncology vol. 15, No. 5, Suppl. 5: 41-45 (1988).
Joffe et al., "A Phase II Study of Recombinant Interferon-beta (r-hIFn-β 1a) in Combination with 5-Fluorouracil (5-FU) in the Treatment of Patients with Advanced Colorectal Carcinoma" *British Journal of Cancer* 75(3), 423-426 (1997).

Schiller et al., "Randomized Phase II-III Trial of Combination Beta and Gamma Interferons and Etoposide and Cisplatin in Inoperable Non-Small Cell Cancer of the Lung" *Journal of the National Cancer Institute* vol. 81, No. 22: 1739-1743 (1989).

Agarwala et al., "Potential Uses of Interferon α2 as Adjuvant Therapy in Cancer" *Annals of Surgical Oncology* 2(4):365-371 (1995).

Cornell et al., "Intralesional Interferon Therapy for Basal Cell Carcinoma" *Journal of the American Academy of Dermatology* vol. 23, No. 4, Part 1: 694-700 (1990).

Recchia et al., "Interferon-β, Retinoids, and Tamoxifen in the Treatment of Metastatic Breast Cancer: A Phase II Study" *Journal of Interferon and Cytokine Research* 15:605-610 (1995).

Salzberg et al., "Involvement of Interferon-system in the Regulation of Cell Growth and Differentiation" *Scanning Microscopy* vol. 4, No. 2: 479-489 (1990).

Martin-Odegard "Interferon Alpha—A New Dimension in Cancer Therapy", Drug News &Perspectives 4(2): 116-117 (1991).

Badie et al., "Stereotactic Delivery of a Recombinant Adenovirus into a C6 Glioma Cell Line in a Rat Brain Tumor Model" Neurosurgery 35(5): 910-916 (1994).

Perez-Cruet et al., "Adenovirus-Mediated Gene Therapy of Experimental Gliomas" J. Neuroscience Research 39: 506-511 (1994).

Fueyo et al. "A Mutant Oncolytic Adenovirus Targeting the Rb Pathway Produces Anti-glioma Effect In Vivo", Oncogene 19: 2-12 (2000).

Geng Y. et al., "Tumor Suppressor Activity of the Human Consensus Type I Interferon Gene", *Cytokine and Molecular Therapy* 1: 289-300 (1995).

Klein M.L. et al., "Structural Characterization of Recombinant Consensus Interferon-α", *Journal of Chromatography* 454: 205-215 (1988).

Tada H. et al., "Systemic IFN-β Gene Therapy Results in Long-term survival in Mice with Established Colorectal Liver Metastases", *The Journal of Clinical Investigation* 108: 83-95 (2001).

Odaka M. et al., "Eradication of Intraperitoneal and Distant Tumor by Adenovirus-mediated Interferon-β Gene Therapy Is Attributable to Induction of Systemic Immunity" *Cancer Research* 61: 6201-6212 (2001).

Wu X. et al., "Development of a Novel Trans-Lentiviral Vector That Affords Predictable Safety", *Molecular Therapy* 2(1): 47-55 (2000).

Abramovich et al., 1994, Cytokine, 6:No. 4 412-424, "The Human Interferon Alpha-Receptor Protein Confers Differential Responses To Human Interferon-Beta Versus Interferon-Alpha Subtypes In Mouse And Hamster Cell Transfectants".

Bramson et al., 1996, Human Gene Therapy, 7:1995-2002, "Direct Intratumoral Injection of an Adenovirus Expressing Interleukin-12 Induces Regression and Long-Lasting Immunity That is Associated With Highly Localized Expression of Interleukin-12".

Domanski et al., 1998, J. of Biological Chemistry, 273:3144-3147, "Differential Use of the BetaL Subunit of the Type I Interferon (IFN) Receptor Determines Signaling Specificity for IFN Alpha2 and IFN Beta".

Dong, Greene, et A1., 1999, Cancer Research, 59:872-879, "Suppression of Angiogenesis, Tumorigenicity, and Metastasis by Human Prostate Cancer Cells Engineered to Produce Interferon-Beta I".

Dong, Juang, et al., 1998, Cancer Immunol. Immunother, 46:137-146, "Suppression of Tumorigenicity and metastasis in murine UV-2237 fibrosarcoma cells by infection with a retroviral vector harboring the interferon-beta gene".

Engelhardt et al., 1994, Human Gene Therapy, 5:1217-1229, "Prolonged Transgene Expression in Cotton Rat Lung with Recombinant Adenoviruses Defective in E2a".

Freeman et al., 1993, Cancer Research, 53:5274-5283, "The "Bystander Effect": Tumor Regression When a Fraction of the Tumor Mass Is Genetically Modified".

Gordon et al., 1983, J. Gen. Virol., 64:2777-2780, "Mouse Interferon Receptors: A Difference in Their Response to Alpha and Beta Interferons".

Howard et al., 1994, Annals of the New York Academy of Sciences, 716:167-187, "Retrovirus-mediated gene transfer of the Human gamma-IFN gene: A Therapay for Cancer".

Hu et al., 1995, J. of Interferon and Cytokine Research, 15:231-234, "Comparison of the In Vitro Host Range of Recombinant met-Interferon-con1, Interferon-alpha2a, and Interferon-Beta".

Johns et al., 1991, Reports, 84:1185-1190, "Antiproliferative Potencies of Interferons on Melanoma Cell Lines and Xenografts Higher Efficacy of Interferon Beta".

Qin et al., 1998, Proc. Natl. Acad. Sci., 95:14411-14416, "Interferon-Beta gene therapy inhibits tumor formation and causes regression of established tumors in immune-deficient mice".

Setoguchi et al., 1994, J. of Investigative Dermatology, 102:415-421, "Ex Vivo and In Vivo Gene Transfer to the Skin Using Replication-Deficient Recombinant Adenovirus Vectors".

Sica et al., 1989, Neurological Research, 17:111-115, "Antiproliferative effect of interferons on human prostate carcinoma cell lines".

Toloza et al., 1997, Annals of Surgical Oncology, 4:70-79, "Transduction of Murine and Human Tumors Using Recombinant Adenovirus Vectors".

Uze et al., 1995, J. of Interferon and Cytokine Research, 15:3-26, "Alpha and GBeta Interferons and Their Receptor and Their Friends and Relations".

Xie et al., 1997, Clinical Cancer Research, 3:2283-2294, "Abrogation of Tumorigenicity and Metastasis of Murine and Human Tumor Cells by Transfection with the Murine IFN-Beta Gene: Possible Role of Nitric Oxide".

Yagi et al., 1994, Biochem. and Molecular Biology International, 32:167-171, "Interferon-Beta Endogenously Produced By Intratumoral Injection of Cationic Liposome Encapsulated Gene: Cytocidal Effect on Glioma Transplanted Into Nude Mouse Brain".

Zhang et al., 1996, Cancer Gene Therapy, 3:31-38, "Gene Therapy With an Adeno-Associated Virus Carrying An Interferon Gene Results in Tumor Growth Suppression and Regression".

Zhang et al., 1996, Proc. Natl. Acad. Sci., 93:4513-4518, "Treatment of a Human Breast Cancer Xenograft with an adenovirus vector containing an interferon gene results in rapid regression due to viral oncolysis and gene therapy".

Pardoll, D., "Immunotherapy with Cytokine Gene-transduced Tumor Cells: the Next Wave In Gene Therapy for Cancer", Current Opinion in Oncology 4, pp. 1124-1129 (1992).

Gansbacher B. et al., "Retroviral Vector-Mediated gamma-Interferon Gene Transfer Into Tumor Cells Generates Potent And Long Lasting Antitumor Immunity" *Cancer Res.* 50(24): 7820-7825 (1990).

Nishihara, K., "A Novel Experimental Approach To Immunotherapy Against Malignant Brain Tumor With The Mouse IFN-gamma Gene Transfer" *Archiv fur Japanische Chirurgie* 58(1): 18-42 (1989), X Abstract only.

Fearon, E. R. et al., "Interleukin-2 Production By Tumor Cells Bypasses T Helper Function In The Generation Of An Antitumor Response" *Cell* 60: 397-403 (1990).

Haddada, H. et al., "Adenoviral Interleukin-2 Gene Transfer Into P815 Tumor Cells Abrogates Tumorigenicity And Induces Anti-Tumoral Immunity In Mice" *Hum. Gene Ther.* 4: 703-711 (1993).

Ohwada, A. et al., "Regional Delivery Of An Adenovirus Vector Containing The *Escherichia coli* Cytosine Deaminase Gene To Provide Local Activation Of 5-Fluorocytosine To Suppress The Growth Of Colon Carcinoma Metastatic To Liver" *Human Gene Ther.* 7: 1567-1576 (1996).

Eastham, J. A. et al., "Prostate Cancer Gene Therapy: Herpes Simplex Virus Thymidine Kinase Gene Transduction Followed By Ganciclovir In Mouse And Human Prostate Cancer Models" *Human Gene Ther.* 7: 515-523 (1996).

Elshami, A. A. et al., "Treatment Of Mesothelioma In An Immunocompetent Rat Model Utilizing Adenovirus Transfer Of The Herpes Simplex Virus Thymidine Kinase Gene" *Human Gene Ther.* 7: 141-148 (1996).

Ko, S. et al., "Molecular Therapy With Recombinant p53 Adenovirus In An Androgen-Independent Metastatic Human Prostate Cancer Model" *Human Gene Ther.* 7: 1683-1691 (1996).

Hirschowitz, E. A. et al., "In Vivo Adenovirus-Mediate Gene Transfer Of The *Escherichia coli* Cytosine Deaminase Gene To Human Colon Carcinoma-Derived Tumors Induces Chemosensitivity To 5-Fluorocytosine" *Human Gene Ther.* 6: 1055-1063 (1995).

Xu, X. et al., "Adenovirus-Mediated Interferon-gamma Transfer Inhibits Growth Of Transplanted HTLV-1 Tax Tumors In Mice" *Human Gene Ther.* 7: 471-477 (1996).

Abe, J. et al., "In Vivo Antitumor Effect Of Cytotoxic T Lymphocytes Engineered To Produce Interferon-gamma By Adenovirus-Mediated Genetic Transduction" *Biochem. Biophys. Res. Comm.* 218: 164-170 (1996).

Riley, D. J. et al., "Adenovirus-Mediated Retinoblastoma Gene Therapy Suppresses Spontaneous Pituitary Melanotroph Tumors In $Rb^{+/-}$ Mice" *Nature Medicine* 2(12): 1316-1321 (1996).

Tepper, R. I. et al., "Murine Interleukin-4 Displays Potent Anti-Tumor Activity In Vivo" *Cell* 57: 503-512 (1989).

Golumbek, P. T. et al., "Treatment Of Established Renal Cancer By Tumor Cells Engineered To Secrete Interleukin-4" *Science* 254: 713-716 (1991).

Asher, A. L. et al., "Murine Tumor Cells Transduced With The Gene For Tumor Necrosis Factor-alpha: Evidence For Paracrine Immune Effects Of Tumor Necrosis Factor Against Tumors" *J. Immunol.* 146: 3227-3234 (1991).

Restifo, N. P. et al., "A Nonimmunogenic Sarcoma Transduced With The cDNA For Interferon-gamma Elicits $CD8^+$ T Cells Against The Wild-Type Tumor: Correlation With Antigen Presentation Capability" *J. Exp. Med.* 175: 1423-1431 (1992).

Spear, M. A. et al., "Targeting Gene Therapy Vectors To CNS Malignancies" *J. NeuroVirol.* 4: 133-147 (1998).

Kuriyama, S. et al., "A Potential Approach For Gene Therapy Targeting Hepatoma Using A Liver-Specific Promoter On A Retroviral Vector" *Cell Struct. Func.* 16(6): 503-510 (1991).

Haddada, H. et al., "Prosepects For Tumor Therapy Following Direct Gene Delivery In Vivo" *Cancer Detect. Preven.* 17(1): 101 (1993).

Culver, K. W. et al., "In Vivo Gene Transfer With Retroviral Vector-Producer Cells For Treatment Of Experimental Brain Tumors" *Science* 256: 1550-1552 (1992).

Boviatsis E. J. et al., "Antitumor Activity And Reporter Gene Transfer Into Rat Brain Neoplasms Inoculated With Herpes Simplex Virus Vectors Defective In Thymidine Kinase Or Ribonucleotide Reductase" *Gene Therapy* 1: 323-331 (1994).

Fueyo, J. et al., "Adenovirus-Mediate *P16/CDKN2* Gene Transfer Induces Growth Arrest And Modifies The Transformed Phenotype Of Glioma Cells" *Oncogene* 12: 103-110 (1996).

Maron, A. et al., "Gene Therapy Of Rate C6 Glioma Using Adenovirus-Mediated Transfer Of The Herpes Simplex Virus Thymidine Kinase Gene: Long-Term Follow-Up By Magnetic Resonance Imaging" *Gene Therapy* 3: 315-322 (1996).

Haj-Ahmad, Y. et al., "Development Of A Helper-Independent Human Adenovirus Vector And Its Use In The Transfer Of The Herpes Simplex Virus Thymidine Kinase Gene" *J. Virol.* 57(1): 267-274 (1986).

Ghosh-Choudhury, G. et al., "Stable Transfer Of A Mouse Dihydrofolate Reductase Gene Into A Deficient Cell Line Using Human Adenovirus Vector" *Biochem. Biophys. Res. Comm.* 147(3): 964-973 (1987).

Ruether, J. E. et al., "Cell-Type Specific Synthesis Of Murine Immunoglobulin μ RNA From An Adenovirus Vector" *Mol. Cell. Biol.* 6(1): 123-133 (1986).

Johnson, D. C. et al., "Abundant Expression Of Herpes Simplex Virus Glycoprotein gB Using An Adenovirus Vector" *Virology* 164: 1-14 (1988).

Azizi, S. A. et al., "Principles Of Treatment Of Malignant Gliomas In Adults: An Overview" *J. NeuroVirol.* 4: 204-216 (1998).

Russell, S. J., "Lymphokine Gene Therapy For Cancer" *Immunology Today* 11(6): 196-200 (1990).

Dachs, G. U. et al., "Targeting Gene Therapy To Cancer: A Review" *Oncology Research* 9: 313-325 (1997).

Venkatesh, L. K. et al., "Selective Induction Of Toxicity To Human Cells Expressing Human Immunodeficiency Virus Type 1 Tat By A Conditionally Cytotoxic Adenovirus Vector" *Proc. Nat. Acad. Sci. USA* 87: 8746-8750 (1990).

Packer, R. J., "Alternative Therapies For Children With Brain Stem Gliomas: Immunotherapy And Gene Therapy" *Pediatric Neurosurgery* 24: 217-222 (1996).

Haddada, H. et al., "Efficient Adenovirus-Mediate Gene Transfer Into Human Blood Monocyte-Derived Macrophages" *Biochem. Biophys. Res. Comm.* 195(3): 1174-1183 (1993).

Zabner, J. et al., "Adenovirus-Mediated Gene Transfer Transiently Corrects The Chloride Transport Defect In Nasal Epithelia Of Patients With Cystic Fibrosis" *Cell* 75: 207-216 (1993).

Bett, A. J. et al., "DNA Sequence Of The Deletion / Insertion In Early Region 3 Of Ad5 D/309" *Virus Research* 39: 75-82 (1995).

Jones, N. et al., "Isolation Of Adenovirus Type 5 Host Range Deletion Mutants Defective For Transformation Of Rat Embryo Cells" *Cell* 17: 683-689 (1979).

Jones, N. et al., "Isolation Of Deletion And Substitution Mutants Of Adenovirus Type 5" *Cell* 13: 181-188 (1978).

Ogura, H. et al., "Implantation Of Genetically Manipulated Fibroblasts Into Mice As Antitumor alpha-Interferon Therapy" *Cancer Res.* 50: 5102-5106 (1990).

Okada, H. et al., "Gene Therapy Against An Experimental Glioma Using Adeno-Associated Virus Vectors" *Gene Therapy* 3: 957-964 (1996).

Clayman, G. et al., "In Vivo Molecular Therapy With *p53* Adenovirus For Microscopic Residual Head And Neck Squamous Carcinoma" *Cancer Res.* 55: 1-6 (1995).

Stratford-Perricaudet, L. et al., "Gene Transfer Into Animals: The Promise Of Adenovirus" *Human Gene Transfer / Colloque INSERM / John Libbey Eurotext Ltd.©* Eds. O. Cohen-Haguenauer, M. Boiron 219: 51-61 (1991).

Stratford-Perricaudet, L. D. et al., "Evaluation Of the Transfer And Expression In Mice Of An Enzyme-Encoding Gene Using A Human Adenovirus Vector" *Hum. Gene Ther.* 1: 241-256 (1990).

Nishihara, K. et al., "Augmentation Of Tumor Targeting In A Line Of Glioma-Specific Mouse Cytotoxic T-Lymphocytes By Retroviral Expression Of Mouse gamma-Interferon Complementary DNA" *Cancer Res.* 48(17): 4730-4735 (1988).

Gansbacher, B. et al., "Interleukin-2 Gene Transfer Into Tumor Cells Abrogates Tumorigenicity And Induces Protective Immunity" *J. Exp. Med.* 172: 1217-1224 (1990).

Drumm, M. L. et al., "Correction Of The Cystic Fibrosis Defect In Vitro By Retrovirus-Mediated Gene Transfer" *Cell* 62: 1227-1233 (1990).

Watanabe, Y. et al., "Exogenous Expression Of Mouse Interferon gamma cDNA In Mouse Neuroblastoma C1300 Cells Results In Reduced Tumorigenicity By Augmented Anti-Tumor Immunity" *Proc. Nat. Acad. Sci. USA* 86: 9456-9460 (1989).

Stephan, D. et al., "Transfection Genique Directe Dans Le Rein De Rat In Vivo" *Archives des Maladies du Coeur et des Vaisseaux* 90(8): 1127-1130 Aug. 1997, X Abstract only.

Stephan, D. et al., "Inhibition Of Vascular Smooth Muscle Cell Proliferation And Intimal Hyperplasia By Gene Transfer Of beta-Interferon" *Mol. Medicine* 3(9): 593-599 Sep. 1997.

Stephan, D. et al., "Le Transfer Du Gene De L'interferon Beta Inhibe La Proliferation Des Cellules Musculaires Lisses In Vitro Et Dans Un Modele Animal De Lesion Arterielle" *Archives des Maladies du Coeur et des Vaisseaux* 90(8): 1121-1125 Aug. 1997, X Abstract only.

Haddada, H. et al., "Gene Therapy Using Adenovirus Vectors" in *Molecular Repertoire of Adenoviruses III* Eds. Capron et al. (Current Topics in Microbiology and Immunology) Springer-Verlag Berlin Heidelberg, pp. 297-306 (1995).

Rozera, C. et al. "Interferon (IFN)-beta Gene Transfer Into TS/A Adenocarcinoma Cells And Comparison With IFN-alpha: Differential Effects On Tumorigenicity And Host Response" *American J. Pathology* 154(4): 1211-1222 (1999).

Rosenfeld, M. A. et al., "Adenovirus-Mediated Transfer Of A Recombinant alpha1-Antitrypsin Gene To The Lung Epithelium In Vivo" *Science* 252: 431-434 (1991).

Chasse, J. et al., "Somatic Gene Therapy Of A Mouse Enzyme Deficiency Using A Recombinant Adenovirus" *J. Cell. Biochem.* Suppl. 13B 174 (Abstract F120) (1989).

Weitzman, M. D. et al., "Adenovirus Vectors in Cancer Gene Therapy" in *The Internet Book of Gene Therapy: Cancer Therapeutics* 17-25 Eds. Sobol and Scanlon © 1995 Appleton & Lange Stamford, CT.
Massie, B. et al., "Construction Of Helper-Free Recombinant Adenovirus That Expresses Polyomavirus Large T Antigen" *Mol. Cell. Biol.* 6(8): 2872-2883 (1986).
Ezzeddine, Z. D. et al., "Selective Killing Of Glioma Cells In Culture And In Vivo By Retrovirus Transfer Of The Herpes Simplex Virus Thymidine Kinase Gene" *New Biol.* 3(6): 608-614 (1991).
Leinwand, L. A. et al., "Gene Transfer Into Cardiac Myocytes In Vivo" *Trends in Cardiovascular Medicine* 1(7): 271-276 (1991).
Dong Z. et al., "Suppression of Tumorigenicity and Metastasis in Murine UV-2237 Fibrosarcoma Cells by Infection with a Retroviral Vector Harboring the Interferon-beta Gene" *Cancer Immunol Immunother* 46: 137-146 (1998).
Bocci V., "Distribution, Catabolism and Pharmacokinetics of Interferons" in "Interferon: in Vivo and Clinical Studies" vol. 4: 47-72, eds. N.B. Finter and R.K. Oldham, Elsever Science Publishers (1985).
Gordon I. et al., "Mouse Interferon Receptors: A Difference in Their Response to α and β Interferons" *J. Gen. Virol.* 64: 2777-2780 (1983).
Uze G. et al., "α and β Interferons and Their Receptor and Their Friends and Relations" *Journal of Interferon and Cytokine Research* 15: 3-26 (1995).
Abramovich C. et al. "Differential Tyrosine Phosphorylation of the IFNAR Chain of the Type I Interferon Receptor and of an Associated Surface Protein in Response to IFN-α and IFN-β" *the EMBO J.* 13: 5871-5877 (1994).
Ferrantini M. et al., "IFN-α1 Gene Expression into a Metastatic Murine Adenocarcinoma (TS/A) Results in CD8+ T-Cell Mediated Tumor Rejection and Development of Antitumor Immunity: Comparitive Studies with IFN-γ-Producing TS/A Cells" *the Journal of Immunology* 153: 4604-4615 (1994).
Yagi et al., "Interferon-BETA endogenously produced by intratumoral injection of cationic liposome-encapsulated gene: cytocidal effect on glioma transplanted into nude mouse brain" *Biochemistry and Molecular Biology International*, vol. 32, 167-171 (1994).
Gorziglia et al., "Elimination of both E1 and E2a from adenovirus vectors further improves prospects for in vivo human gene therapy" *J. Virol.* 70: 4173-4178 (1996).
Hardy et al., "Construction of adenovirus vectors through Cre-lox recombination" *J. Virol.* vol. 71: 1842-1849 (1997).
Anderson, "Human gene therapy" *Nature* 392: 25-30 (1998).
Deonarain, "Ligand-targeted receptor-mediated vectors for gene delivery" *Exp. Opin. Ther. Patents*, vol. 8, pp. 53-69 (1998).
Verma et al., "Gene Therapy Promises, problems and prospects", *Nature* vol. 389, pp. 239-242 (1997).
Crystal, "Transfer of gene to humans: early lessons and obstacles to success" *Science* 270: 404-410 (1995).
Miller et al., "Targeted vectors for gene therapy" *FASEB J.* vol. 9: 190-199 (1995).
Lauret, E., et al., "Development of Methods for Somatic Cell Gene Therapy Directed Against Viral Diseases, Using Retroviral Vectors Carrying the Murine or Human Interferon-β Coding Sequence: Establishment of the Antiviral State in Human Cells," *Hum. Gen. Ther.,*, 4:567-577, Mary Ann Liebert, Inc. (1993).
Asselbergs, F.A.M., et al., "Structural Characterization of the Proteins Encoded by Adenovirus Early Region 2A," *J. Mol. Biol.* 163:177-207, Academic Press (1983).
Bridge, E. and Ketner, G., "Redundant Control of Adenovirus Late Gene Expression by Early Region 4," *J. Virol.* 63:631-638, American Society for Microbiology (1989).
DeLong, P., et al., "Use of Cylooxygenase-2 Inhibition to Enhance the Efficacy of Immunotherapy," *Cancer Res.* 63:7845-7852, The American Association for Cancer Research (Nov. 2003).
Engelhardt, J.F., et al., "Ablation of *E2A* in recombinant adenoviruses improves transgene persistence and decreases inflammatory response in mouse liver," *Proc. Natl. Acad. Sci. USA* 91:6196-6200, The National Academy of Sciences (1994).
Lu, W., et al., "Eradication of Primary Murine Fibrosarcomas and Induction of Systemic Immunity by Adenovirus-mediated Interferon β Gene Therapy," *Cancer Res.* 59:5202-5208, The American Association for Cancer Research (Oct. 1999).
Setoguchi, Y., et al., "Adenovirus vector," *Igaku no Ayumi 175*:612-618, Ishiyaku (1995).
STN*Easy*/CAplus Database, Accession No. 1996:12899, English language abstract of document NPL6, Setoguchi, Y., et al., "Adenovirus vector," *Igaku no Ayumi 175*:612-618, Ishiyaku (1995).
Watanabe, Y., "Cancer gene therapy by IFN gene transfer," *Tanpakushitsu Kakusan Koso 40*:2700-2708, Maruzen Company Ltd. (1995).
STN*Easy*/CAplus Database, Accession No. 1996:225, English language abstract of document NPL8, Watanabe, Y., "Cancer gene therapy by IFN gene transfer," *Tanpakushitsu Kakusan Koso 40*:2700-2708, Maruzen Company Ltd. (1995).
Wilderman, M.J., et al., "Intrapulmonary IFN-β Gene Therapy Using an Adenoviral Vector Is Highly Effective in a Murine Orthotopic Model of Bronchogenic Adenocarcinoma of the Lung," *Cancer Res.* 65:8379-8387, The American Association for Cancer Research (Sep. 2005).
Patents Abstracts of Japan, English language abstract of, JP 57-130998 A, document FP1, 1982.
Patents Abstracts of Japan, English language abstract of JP 8-238092 A, document FP3, 1996.

* cited by examiner

US 7,256,181 B2

METHODS AND COMPOSITIONS FOR THERAPIES USING GENES ENCODING SECRETED PROTEINS SUCH AS INTERFERON-BETA

This application is a continuation of U.S. application Ser. No. 09/512,946, filed Feb. 25, 2000, now U.S. Pat. No. 6,696,423 (issued on Feb. 24, 2004), which is a continuation of PCT application number PCT/US98/17606, filed 25 Aug. 1998, which claims benefit of United States provisional application No. 60/057,254, filed on 29 Aug. 1997. The disclosures of U.S. application Ser. No. 09/512,946, PCT application number PCT/US98/17606 and United States provisional application number 60/057,254 are incorporated by reference herein.

FIELD OF THE INVENTION

This invention relates to gene therapy. More specifically, the present invention relates to delivery of DNA encoding secreted proteins such as interferon proteins in humans and animals.

BACKGROUND OF THE INVENTION

Interferons (also referred to as "IFN" or "IFNs") are proteins having a variety of biological activities, some of which are antiviral, immunomodulating and antiproliferative. They are relatively small, species-specific, single chain polypeptides, produced by mammalian cells in response to exposure to a variety of inducers such as viruses, polypeptides, mitogens and the like. Interferons protect animal tissues and cells against viral attack and are an important host defense mechanism. In most cases, interferons provide better protection to tissues and cells of the kind from which they have been produced than to other types of tissues and cells, indicating that human-derived interferon could be more efficacious in treating human diseases than interferons from other species.

There are several distinct types of human interferons, generally classified as leukocyte (interferon-alpha [α]), fibroblast (interferon-beta [β]) and immune (interferon-gamma [γ]), and a large number of variants thereof. General discussions of interferons can be found in various texts and monographs including: The Interferon System (W. E. Stewart, II, Springer-Verlag, N.Y. 1979); and Interferon Therapy (World Health Organization Technical Reports Series 676, World Health Organization, Geneva 1982), incorporated herein by reference.

Interferons have potential in the treatment of a large number of human cancers since these molecules have anticancer activity which acts at multiple levels. First, interferon proteins can directly inhibit the proliferation of human tumor cells. The anti-proliferative activity is also synergistic with a variety of approved chemotherapeutic agents such as cis-platin, 5FU and taxol. Secondly, the immunomodulatory activity of interferon proteins can lead to the induction of an anti-tumor immune response. This response includes activation of NK cells, stimulation of macrophage activity and induction of MHC class I surface expression leading to the induction of anti-tumor cytotoxic T lymphocyte activity. Moreover, some studies further indicate that IFN-β protein may have anti-angiogenic activity. Angiogenesis, new blood vessel formation, is critical for the growth of solid tumors. Evidence indicates that IFN-β may inhibit angiogenesis by inhibiting the expression of pro-angiogenic factors such as bFGF and VEGF. Lastly, interferon proteins may inhibit tumor invasiveness by affecting the expression of enzymes such as collagenase and elastase which are important in tissue remodeling.

Interferons also appear to have antiviral activities that are based on two different mechanisms. For instance, type I interferon proteins (α and β) can directly inhibit the replication of human hepatitis B virus ("HBV") and hepatitis C virus ("HCV"), but can also stimulate an immune response which attacks cells infected with these viruses.

Specifically, and despite its potential therapeutic value, interferon proteins have only had limited clinical success against viral hepatitis and solid tumors. IFN-α has been approved for the treatment of both HBV and HCV; however, the response rate in both cases is only approximately 20%. While interferon proteins have been approved for the treatment of some cancers such as lymphomas, leukemias, melanoma and renal cell carcinoma, the majority of clinical trials in which interferons are used alone or in combination with conventional chemotherapeutic agents in the treatment of solid tumors have been unsuccessful.

The method of administering interferon is an important factor in the clinical application of this important therapeutic agent. Systemic administration of interferon protein by either intravenous, intramuscular or subcutaneous injection has been most frequently used with some success in treating disorders such as hairy cell leukemia, Acquired Immune Deficiency Syndrome (AIDS) and related Kaposi's sarcoma. It is known, however, that proteins in their purified form are especially susceptible to degradation. In particular, for interferon-beta, the primary mechanism(s) of interferon degradation in solution are aggregation and deamidation. The lack of interferon stability in solutions and other products has heretofore limited its utility. Furthermore, following parenteral interferon protein administration (intramuscular, subcutaneous or intravenous) the clearance rate of interferon protein is very rapid. Therefore, parenteral protein administration may not allow the localization of sufficient interferon at the active site (the solid tumor, or, in the case of hepatitis, the liver). The amount of interferon that can be given parenterally in patients is limited by the side-effects observed at high interferon doses. A more effective therapy is clearly needed.

SUMMARY OF THE INVENTION

This application is directed toward eliminating the problems associated with delivering a secreted protein such as interferon protein as a therapeutic. The present invention is directed to a method of interferon therapy in which the gene encoding the secreted protein rather than the protein itself, is delivered.

Accordingly, it is one object of the instant invention to provide a method of gene therapy based on the use of genetically engineered cells and to the use thereof for delivering a secreted protein such as an interferon to a mammalian recipient. The instant invention satisfies these and other objects by providing methods for forming a cell expression system, the expression system produced thereby and pharmaceutical compositions containing the same. The cell expression system expresses a gene encoding one or more secreted proteins and is useful as a vehicle for delivering the gene product to the mammalian recipient in situ. In a preferred embodiment, the mammalian recipient is a human.

In one embodiment of the invention, a cell expression system is described for expressing in a cell of a mammalian recipient in vivo, an interferon protein for treating a condition. The expression system comprises a cell of the same species as the mammalian recipient and an expression vector contained therein for expressing the interferon protein. Preferably, the mammalian recipient is a human and the expression vector comprises a viral vector.

In another embodiment, the expression system comprises a plurality of cells of the same species as the mammalian recipient and an expression vector contained therein for expressing the secreted protein. The expression vector is contained within only a portion of the plurality of cells. Preferably, at least 0.3% by number of the cells contain the vector. The preferred secreted protein is an interferon and the most preferred interferons are alpha, beta, gamma and consensus interferon, with beta interferon being the most preferred.

In other embodiments, the cell expression system comprises a plurality of cancer cells and at least a portion of the cancer cells contain an adenoviral vector having an isolated polynucleotide encoding, upon expression, an interferon. In this cell expression system, the adenoviral vectors are selected from the group consisting of: (a) an adenoviral vector having a deletion and/or mutation in its E1 gene; (b) an adenoviral vector having a deletion and/or mutation in its E2a gene, said vector expressing human interferon-beta; (c) an adenoviral vector having a deletion and/or mutation in both its E1 and E4 genes, and (d) an adenoviral vector having a deletion of all of its genes; said vector expressing human interferon-beta.

A pharmaceutical composition for delivery of a secreted protein to a site of a mammalian recipient, is also encompassed within the invention. The composition comprises a carrier and a plurality of genetically modified cells of the same species as the mammalian recipient and at least a portion of the cells contain an expression vector for expressing an effective amount of the secreted protein. The preferred secreted protein is an interferon. The composition encompasses compositions for both in vivo and ex vivo delivery.

A method for making an ex vivo gene therapy pharmaceutical preparation for administration to a mammalian recipient is another embodiment. The method includes the steps of: (a) forming a plurality of cells of the same species as the mammalian recipient, (b) introducing an expression vector for expressing a secreted protein into at least one cell of the plurality to form at least one genetically modified cell and (c) placing the at least one genetically modified cell in a pharmaceutically acceptable carrier to obtain a pharmaceutical preparation that is suitable for administration to a site of the mammalian recipient.

Another embodiment of the invention is a method for gene therapy, which comprises genetically modifying at least one cell of a mammalian recipient via the steps of (a) introducing an expression vector for expressing a secreted protein into at least one cell to form at least one genetically modified cell and (b) allowing the genetically modified cell to contact a site of the mammalian recipient. This method may further comprise the step of removing at least one cell from the mammalian recipient prior to the step of introducing the expression vector. In yet another embodiment, the step of introducing the vector comprises introducing a vector to only a portion of the plurality of cells.

A method of ex vivo gene therapy is encompassed by the invention and includes the steps of removing a plurality of cells from a subject; administering a recombinant adenovirus to at least one cell of the plurality of cells, such that there exists an excess of cells not containing the adenovirus. The adenovirus can have a deletion in its E1 gene and includes an isolated polynucleotide encoding a secreted protein. The plurality of cells is reintroduced back into the subject.

In a method of in vivo gene therapy, the steps include administering an adenoviral vector that includes an isolated polynucleotide encoding human interferon-beta (β) protein directly into a cell of a subject without first removing said cell from the subject. The in vivo and ex vivo methods allow for topical, intraocular, parenteral, intranasal, intratracheal, intrabronchial, intramuscular, subcutaneous, intravenous, and intraperitoneal administration.

The present invention has several advantages. Interferon gene therapy may allow for very high local interferon concentrations with low systemic levels. This could result in greater efficacy with lower side-effects. Also, interferons delivered by gene therapy would be present at a fairly constant level, unlike the situation observed in interferon protein therapy in which very high interferon "bursts" or peaks in protein concentration (which could lead to toxicity) that occur after protein injection, are followed by very low levels in which the interferon concentration is likely to be too low to be effective.

Patient convenience is also a critical factor. While frequent injections of interferon protein are necessary, a single administration, or a few infrequent administrations, of a vector expressing the interferon gene could provide long-term stable production of the protein. Gene therapy could allow the delivery of interferons in a controlled manner to a distinct target organ or tumor. An autocrine system can be established in which the same cells express, secrete and take up the interferon. Thus, very high local doses can be achieved. These high doses cannot be achieved by parenteral protein administration due to toxicity problems.

Since interferon proteins are secreted out of cells, every cell in a tumor or in the hepatitis-infected liver need not be transduced by the interferon gene. Those cells which do not take up the gene will be affected by neighboring cells (the so-called "bystander effect") which have the gene and secrete the interferon protein. This is a significant finding and is likely to have dramatic effects on treatment regimens since not every cell in a tumor mass or in an organ need contain an expression vector.

Lastly, parenteral interferon administration has been shown to lead to the generation of anti-interferon antibodies. It may be that this potentially neutralizing antibody response can be lessened following introduction of the interferon gene to a distinct local region. Besides the local expression, the interferon expressed will be produced by endogenous human cells and, therefore, will be more natural in its structure and glycosylation and, possibly, less immunogenic than interferon protein produced in bacteria, yeast or Chinese hamster ovary cells and then purified and injected parenterally.

These and other aspects of the invention as well as various advantages and utilities will be more apparent with reference to the detailed description of the preferred embodiments and to the accompanying drawings.

DESCRIPTION OF THE PREFERRED EMBODIMENTS

Figure 1A:
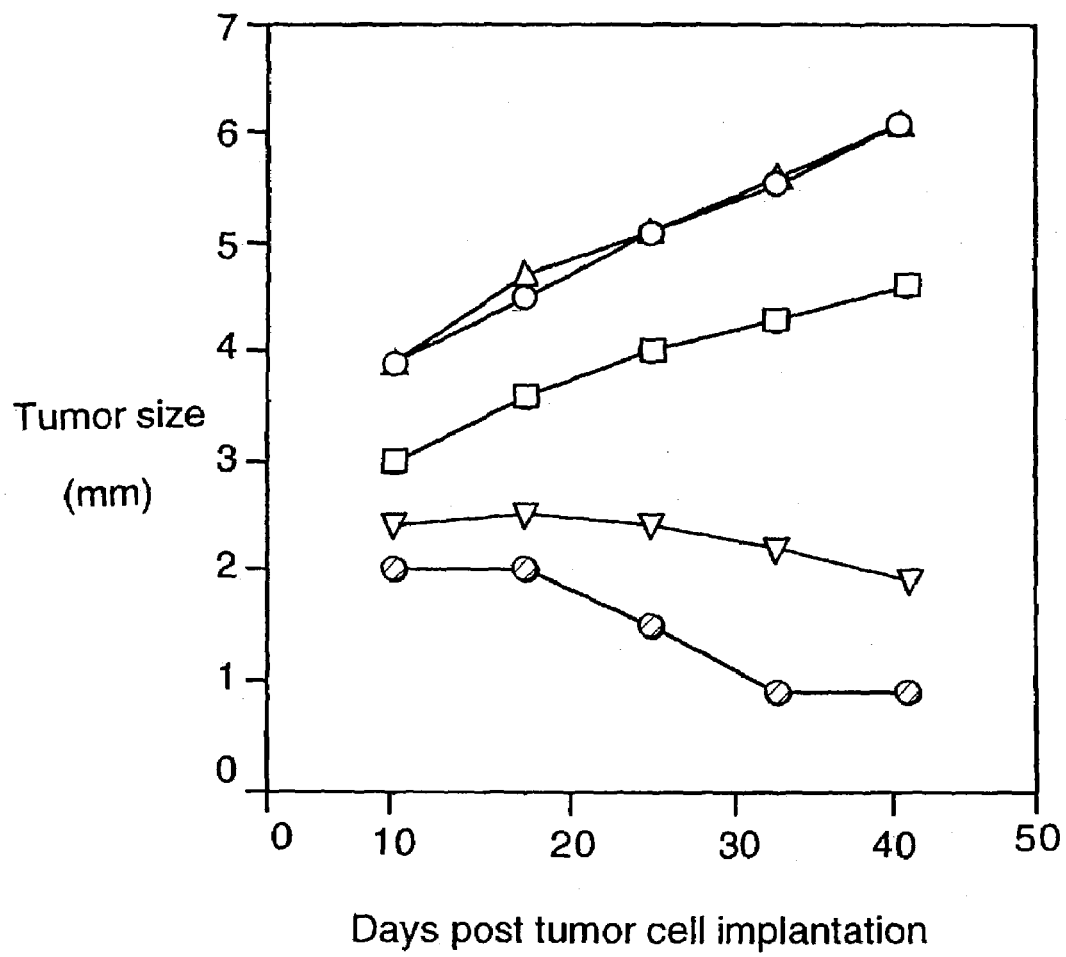
FIG. 1. (A) Either uninfected MDA-MB-468 (-○-) or cells infected with H5.110hIFNβ cells at 0.01% (-Δ-), 0.03% (-□-), 0.1% (-∇-), or 0.3% (-⊘-) were injected subcutaneously into the flanks of nude mice and mean tumor size was plotted versus the time following tumor cell implantation (B) Kaplan-Meir plot showing the percentage survival of mice over the observation period of 109 days. Uninfected cells (-○-); H5.100hIFNβ infected cells at 0.01% (-Δ-); 0.03% (-□-), 0.1% (-∇-); 0.3% (-⊘-).

The present invention is based, in part, on development of an ex vivo gene therapy method that uses a cell that (1) can be easily removed from the patient, (2) can be modified in vitro by introduction of genetic material; (3) can be conveniently implanted in the recipient; (4) is non-thrombogenic; and (5) can be implanted into the recipient in large numbers. The disclosed in vivo gene therapy method uses a cell that (1) is present in the recipient and (2) can be modified in situ to express isolated genetic material. The genetically modified cell includes regulatory elements for controlling the amount of genetic material expressed.

The genetically modified cells will survive and continue to produce the expressed material in situ for an amount of time necessary for the expressed material to have a beneficial (i.e., therapeutic) effect, without interfering with the normal function of the tissue in which the cells are located.

Preferably, the expressed material is a secreted protein (defined below). Most preferably, the secreted protein is an interferon. Indeed, although interferons are the most preferred therapeutic agent, a general principle applicable to gene therapy with any secreted protein has been found. We have found that, due to the fact that secreted proteins such as interferons are released from the cells in which they have been expressed, every cell in a tumor mass or in, for instance, a hepatitis-infected liver need not be transduced by the "secreted protein" gene. Those cells which do not take up the gene will be affected by neighboring cells which have the gene and secrete the protein (i.e., the so-called "bystander effect"). Although gene therapy is described with isolated polynucleotides that encode, upon expression, for interferons, any secreted protein (as defined below) has potential in the present method and compositions.

All citations recited in this document are incorporated herein by reference.

I. Definitions:

"Gene therapy"—a procedure in which a disease phenotype is corrected through the introduction of genetic information into the affected organism.

"ex vivo gene therapy"—a procedure in which cells are removed from a subject and cultured in vitro. A polynucleotide such as a functional gene is introduced into the cells in vitro, the modified cells are expanded in culture, and then reimplanted in the subject.

"in vivo gene therapy"—a procedure in which target cells are not removed from the subject. Rather, the transferred polynucleotide (e.g., a gene encoding, upon expression, for an interferon) is introduced into cells of the recipient organism in situ, that is, within the recipient. In vivo gene therapy has been examined in several animal models and recent publications have reported the feasibility of direct gene transfer in situ into organs and tissues.

"condition amenable to gene therapy"—embraces conditions such as genetic diseases (i.e., a disease condition that is attributable to one or more gene defects), acquired pathologies (i.e., a pathological condition which is not attributable to an inborn defect), cancers and prophylactic processes (i.e., prevention of a disease or of an undesired medical condition).

"acquired pathology"—refers to a disease or syndrome manifested by an abnormal physiological, biochemical, cellular, structural, or molecular biological state.

"polynucleotide"—a polymer of nucleic acid monomeric units, the monomeric units being either ribonucleic acids (RNA), deoxyribonucleic acids (DNA), or combinations of both. The four DNA bases are adenine (A), guanine (G), cytosine (C) and thymine (T). The four RNA bases are A, G, C, and uracil (U).

"isolated"—when applied to polynucleotide sequences of genes that encode an interferon, means an RNA or DNA polynucleotide, portion of genomic polynucleotide, cDNA or synthetic polynucleotide which, by virtue of its origin or manipulation: (i) is not associated with all of a polynucleotide with which it is associated in nature (e.g., is present in a host cell as a portion of an expression vector); or (ii) is linked to a nucleic acid or other chemical moiety other than that to which it is linked in nature; or (iii) does not occur in nature. By "isolated" it is further meant a polynucleotide sequence: (i) amplified in vitro by, for example, polymerase chain reaction (PCR); (ii) chemically synthesized; (iii) recombinantly produced by cloning; or (iv) purified, as by cleavage and gel separation.

Thus, an "isolated" interferon polynucleotide includes, for example, a non-naturally occurring nucleic acid that can be transcribed into anti-sense RNA, as well as a gene encoding an interferon protein which is not expressed or is expressed at biologically insignificant levels in a naturally-occurring cell. To illustrate, a synthetic or natural gene encoding human interferon-beta 1a would be considered "isolated" with respect to human brain cells since the latter cells do not naturally express interferon-beta 1a. Still another example of an "isolated polynucleotide" is the introduction of only part of an interferon gene to create a recombinant gene, such as combining an inducible promoter with an endogenous interferon coding sequence via homologous recombination.

"gene"—a DNA sequence (i.e., a linear array of nucleotides connected to each other by 3'-5' pentose phosphodiester bonds) which encodes through its mRNA an amino acid sequence of a specific protein.

"transcription"—the process of producing mRNA from a gene.

"translation"—the process of producing a protein from mRNA.

"expression"—the process undergone by a DNA sequence or a gene to produce a protein, combining transcription and translation.

"inhibiting growth"—as used herein this term refers to both the inhibition of target cell (i.e., tumor) growth and inhibition of the transformed phenotype (as measured by, for example, changes in morphology).

"amino acid"—a monomeric unit of a peptide, polypeptide, or protein. There are twenty L-isomers of amino acids. The term also includes analogs of the amino acids and D-isomers of the protein amino acids and their analogs.

"protein"—any polymer consisting essentially of any of the 20 protein amino acids, regardless of its size. Although "polypeptide" is often used in reference to relatively large polypeptides, and "peptide" is often used in reference to small polypeptides, usage of these terms in the art overlaps and is varied. The term "protein" as used herein refers to peptides, proteins and polypeptides, unless otherwise noted.

"secreted protein"—a protein which is transported from the inside of a cell to the exterior of the cell; among secreted proteins are a large number of growth factors and immunomodulator proteins such as the various interferons ($\alpha$, $\beta$, $\gamma$), interleukins such as IL-1, -2, -4, -8, and -12 and growth factors such as GM-CSF, G-CSF.

"genetic fusion"—refers to a co-linear, covalent linkage of two or more proteins via their individual peptide backbones, through genetic expression of a polynucleotide molecule encoding those proteins.

"mutant"—any change in quality or structure of genetic material of an organism, in particular any change (i.e., deletion, substitution, addition, or alteration) in a wild type interferon gene or any change in a wild type interferon protein.

"wild type"—the naturally-occurring polynucleotide or amino acid sequence of an interferon gene or interferon protein, respectively, as it exists in vivo.

"standard hybridization conditions"—salt and temperature conditions substantially equivalent to 0.5×SSC to about 5×SSC and 65 degrees C. for both hybridization and wash. The term "standard hybridization conditions" as used herein is therefore an operational definition and encompasses a range of hybridizations. Higher stringency conditions may, for example, include hybridizing with plaque screen buffer (0.2% polyvinylpyrrolidone, 0.2% Ficoll 400; 0.2% bovine serum albumin, 50 mM Tris-HCl (pH 7.5); 1 M NaCl; 0.1% sodium pyrophosphate; 1% SDS); 10% dextran sulphate, and 100 ug/ml denatured, sonicated salmon sperm DNA at 65 degrees C. for 12-20 hours, and washing with 75 mM NaCl/7.5 mM sodium citrate (0.5×SSC)/1% SDS at 65 degrees C. Lower stringency conditions may, for example, include hybridizing with plaque screen buffer, 10% dextran sulphate and 110 ug/ml denatured, sonicated salmon sperm DNA at 55 degrees C. for 12-20 hours, and washing with 300 mM NaCl/30 mM sodium citrate (2.0×SSC)/1% SDS at 55 degrees C.

"expression control sequence"—a sequence of nucleotides that controls and regulates expression of genes when operatively linked to those genes.

"operatively linked"—a polynucleotide sequence (DNA, RNA) is operatively linked to an expression control sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the polynucleotide sequence under the control of the expression control sequence and production of the desired interferon encoded by the isolated polynucleotide sequence.

"expression vector"—a polynucleotide, most commonly a DNA plasmid (but which also includes a virus) which allows expression of at least one gene when the expression vector is introduced into a host cell. The vector may, or may not, be able to replicate in a cell.

"tumor"—any undesirable proliferation of cells. Such growth includes malignant and non-malignant, solid or fluid tumors, carcinomas, myelomas, sarcomas, leukemias, lymphomas and other cancerous, neoplastic or tumorigenic diseases.

"genetically modified cell" (also called a "cell expression system")—comprises a cell and an expression vector for expressing the interferon protein. For ex vivo purposes, the genetically modified cells are suitable for administration to a mammalian recipient, where they replace or co-exist with the endogenous cells of the recipient. For in vivo purposes, the cells are created inside the recipient.

The instant invention also provides various methods for making and using the above-described genetically-modified cells. In particular, the invention provides a method for genetically modifying cell(s) of a mammalian recipient ex vivo and administering the genetically modified cells to the mammalian recipient. In a preferred embodiment for ex vivo gene therapy, the cells are autologous cells, i.e., cells removed from the mammalian recipient. As used herein, the term "removed" means a cell or a plurality of cells that have been removed from their naturally-occurring in vivo location. Methods for removing cells from a patient, as well as methods for maintaining the isolated cells in culture are known to those of ordinary skill in the art (Stylianou, E., et al., *Kidney Intl.* 37:1563-1570 (1992); Hjelle, J. H., et al., *Peritoneal Dialysis Intl.* 9: 341-347 (1989); Heldin, P. *Biochem. J.* 283: 165-170 (1992); Di Paolo, N., et al., *Int. J. Art. Org.* 12: 485-501 (1989); Di Paolo, N., et al., *Clinical Nephrol.* 34: 179-184 (1990); Di Paolo, N., et al., *Nephron* 57: 323-331 (1991)). All patents, patent applications and publications mentioned in the Detailed Description of the Invention, herein, both supra and infra, are incorporated herein by reference. ps II. Isolated, Interferon Polynucleotides An "interferon" (also referred to as "IFN") is a small, species-specific, single chain polypeptide, produced by mammalian cells in response to exposure to a variety of inducers such as viruses, polypeptides, mitogens and the like. The most preferred interferons are in recombinant form and recombinant DNA methods for producing proteins including the various interferons are known and are not intended to limit the invention in any way. See for example, U.S. Pat. Nos. 4,399,216, 5,149,636, 5,179,017 (Axel et al) and 4,470,461 (Kaufman). Recombinant forms of interferon-alpha, beta, gamma and consensus interferon have been produced. Forms of interferon may be expressed from cells containing polynucleotide sequences encoding variants such as cysteine-depleted mutants (e.g., for interferon-beta) and methionine-depleted mutants. Other modifications may take place through the post-translational processing systems of the host cell. The exact chemical structure of a particular interferon will therefore depend on several factors and is not intended to limit the scope of the invention. All such interferon proteins included in the formulations described herein will retain their bioactivity when placed in suitable environmental conditions.

Preferred polynucleotides that may be used in the present methods of the invention are derived from the wild-type interferon gene sequences of various vertebrates, preferably mammals and are obtained using methods that are well-known to those having ordinary skill in the art. See, for example: U.S. Pat. No. 5,641,656 (issued Jun. 24, 1997: DNA encoding avian type I interferon proprotein and mature avian type I interferon), U.S. Pat. No. 5,605,688 (Feb. 25, 1997—recombinant dog and horse type I interferons); U.S. Pat. No. 5,554,513 (Sep. 10, 1996; DNA sequence which codes for human interferon-beta2A); U.S. Pat. No. 5,541,312; Jul. 30, 1996—DNA which codes for human fibroblast beta -2 interferon polypeptide); U.S. Pat. No. 5,231,176 (Jul. 27, 1993, DNA molecule encoding a human leukocyte interferon); ); U.S. Pat. No. 5,071,761 (Dec. 10, 1991, DNA sequence coding for sub-sequences of human lymphoblastoid interferons LyIFN-alpha-2 and LyIFN-alpha -3); U.S. Pat. No. 4,970,161 (Nov. 13, 1990, DNA sequence coding for human interferon-gamma); U.S. Pat. No. 4,738,931 (Apr. 19, 1988, DNA containing a human interferon beta gene); U.S. Pat. No. 4,695,543 (Sep. 22, 1987, human alpha-interferon Gx-1 gene and U.S. Pat. No. 4,456,748 (Jun. 26, 1984, DNA encoding sub-sequences of different, naturally, occurring leukocyte interferons).

Mutant members of the interferon family of genes may be used in accordance with this invention. Mutations in the wild-type interferon polynucleotide sequence are developed using conventional methods of directed mutagenesis, known to those of ordinary skill in the art. The term "mutant" is also meant to encompass genetic fusions so that the following interferon sequences, incorporated herein by reference, would all be considered "mutant" sequences:

U.S. Pat. No. 5,273,889 (Dec. 28, 1993, DNA construct comprising gamma-interferon gene linked to a sequence encoding an immunogenic leukotoxin); U.S. Pat. No. 4,959,314 (Sep. 25, 1990, Gene having a DNA sequence that encodes a synthetic mutein of a biologically active native protein); U.S. Pat. No. 4,929,554 (May 29, 1990, DNA encoding des-CYS-TYR-CYS recombinant human immune interferon); U.S. Pat. No. 4,914,033 (Apr. 3, 1990, DNA molecule encoding a modified beta interferon comprising a beta interferon); and U.S. Pat. No. 4,569,908 (Feb. 11, 1986, DNA having a nucleotide sequence that encodes a multiclass hybrid interferon polypeptide).

Moreover, the isolated polynucleotides described in these patents can be altered to provide for functionally equivalent polynucleotides. A polynucleotide is "functionally equivalent" compared with those of the above sequences if it satisfies at least one of the following conditions:

(a): the "functional equivalent" is a polynucleotide that hybridizes to any of the foregoing sequences under standard hybridization conditions and/or is degenerate to any of the foregoing sequences. Most preferably, it encodes a mutant interferon having the therapeutic activity of a wild type interferon;

(b) the "functional equivalent" is a polynucleotide that codes on expression for an amino acid sequence encoded by any of the polynucleotides of the foregoing interferon sequences.

In summary, the term "interferon" includes, but is not limited to, the agents listed above as well as their functional equivalents. As used herein, the term "functional equivalent" therefore refers to an interferon protein or a polynucleotide encoding the interferon protein that has the same or an improved beneficial effect on the mammalian recipient as the interferon of which is it deemed a functional equivalent. As will be appreciated by one of ordinary skill in the art, a functionally equivalent protein can be produced by recombinant techniques, e.g., by expressing a "functionally equivalent DNA". Accordingly, the instant invention embraces interferons encoded by naturally-occurring DNAs, as well as by non-naturally-occurring DNAs which encode the same protein as encoded by the naturally-occurring DNA. Due to the degeneracy of the nucleotide coding sequences, other polynucleotides may be used to encode interferons. These include all, or portions of the above sequences which are altered by the substitution of different codons that encode the same amino acid residue within the sequence, thus producing a silent change. Such altered sequences are regarded as equivalents of these sequences. For example, Phe (F) is coded for by two codons, TTC or TTT, Tyr (Y) is coded for by TAC or TAT and His (H) is coded for by CAC or CAT. On the other hand, Trp (W) is coded for by a single codon, TGG. Accordingly, it will be appreciated that for a given DNA sequence encoding a particular interferon there will be many DNA degenerate sequences that will code for it. These degenerate DNA sequences are considered within the scope of this invention.

Consensus interferon is also included within this definition. As employed herein, "consensus interferon" is a non-naturally occurring polypeptide, which predominantly includes those amino acid residues that are common to all naturally-occurring human interferon subtype sequences and which include, at one or more of those positions where there is no amino acid common to all subtypes, an amino acid which predominantly occurs at that position and in no event includes any amino acid residue which is not extant in that position in at least one naturally-occurring subtype. Consensus interferon sequences encompass consensus sequences of any of the above-referenced interferons provided that they have subtype sequences. Exemplary consensus interferons are disclosed in U.S. Pat. Nos. 4,695,623 and 4,897,471 (Amgen). DNA sequences encoding consensus interferon may be synthesized as described in these patents or by other standard methods. Consensus interferon polypeptides are preferably the products of expression of manufactured DNA sequences, transformed or transfected into hosts, as described herein. That is, consensus interferon is preferably recombinantly produced. Such materials may be purified by procedures well known in the art.

The above-disclosed interferons and conditions amenable to gene replacement therapy are merely illustrative and are not intended to limit the scope of the instant invention. The selection of a suitable interferon for treating a known condition is deemed to be within the scope of one of ordinary skill of the art without undue experimentation.

III. Methods for Introducing Polynucleotide Sequences of Secreted Proteins into Cells The term "transformation" or "transform" refers to any genetic modification of cells and includes both "transfection" and "transduction".

As used herein, "transfection of cells" refers to the acquisition by a cell of new genetic material by incorporation of added DNA. Thus, transfection refers to the insertion of nucleic acid (e.g., DNA) into a cell using physical or chemical methods. Several transfection techniques are known to those of ordinary skill in the art including: calcium phosphate DNA co-precipitation (Methods in Molecular Biology, Vol. 7, Gene Transfer and Expression Protocols, Ed. E. J. Murray, Humana Press (1991)); DEAE-dextran (supra); electroporation (supra); cationic liposome-mediated transfection (supra); and tungsten particle-facilitated microparticle bombardment (Johnston, S. A., *Nature* 346: 776-777 (1990)); and strontium phosphate DNA co-precipitation (Brash D. E. et al. *Molec. Cell. Biol.* 7: 2031-2034 (1987). Each of these methods is well represented in the art.

In contrast, "transduction of cells" refers to the process of transferring nucleic acid into a cell using a DNA or RNA virus. One or more isolated polynucleotide sequences encoding one or more interferon proteins contained within the virus may be incorporated into the chromosome of the transduced cell. Alternatively, a cell is transduced with a virus but the cell will not have the isolated polynucleotide incorporated into its chromosomes but will be capable of expressing interferon extrachromosomally within the cell.

According to one embodiment, the cells are transformed (i.e., genetically modified) ex vivo. The cells are isolated from a mammal (preferably a human) and transformed (i.e., transduced or transfected in vitro) with a vector containing an isolated polynucleotide such as a recombinant gene operatively linked to one or more expression control sequences for expressing a recombinant secreted protein (e.g., an interferon). The cells are then administered to a mammalian recipient for delivery of the protein in situ. Preferably, the mammalian recipient is a human and the cells to be modified are autologous cells, i.e., the cells are isolated from the mammalian recipient. The isolation and culture of cells in vitro has been reported According to another embodiment, the cells are transformed or otherwise genetically modified in vivo. The cells from the mammalian recipient (preferably a human), are transformed (i.e., transduced or transfected) in vivo with a vector containing isolated polynucleotide such as a recombinant gene operatively linked to one or more expression control sequences for expressing a secreted protein (i.e., recombinant interferon) and the protein is delivered in situ.

The isolated polynucleotides encoding the secreted protein (e.g., a cDNA encoding one or more therapeutic interferon proteins) is introduced into the cell ex vivo or in vivo by genetic transfer methods, such as transfection or transduction, to provide a genetically modified cell. Various expression vectors (i.e., vehicles for facilitating delivery of the isolated polynucleotide into a target cell) are known to one of ordinary skill in the art.

Typically, the introduced genetic material includes an isolated polynucleotide such as an interferon gene (usually in the form of a cDNA comprising the exons coding for the interferon) together with a promoter to control transcription of the new gene. The promoter characteristically has a specific nucleotide sequence necessary to initiate transcription. Optionally, the genetic material could include intronic sequences which will be removed from the mature transcript by RNA splicing. A polyadenylation signal should be present at the 3' end of the gene to be expressed. The introduced genetic material also may include an appropriate secretion "signal" sequence for secreting the therapeutic gene product (i.e., an interferon) from the cell to the extracellular milieu.

Optionally, the isolated genetic material further includes additional sequences (i.e., enhancers) required to obtain the desired gene transcription activity. For the purpose of this discussion an "enhancer" is simply any non-translated DNA sequence which works contiguous with the coding sequence (in cis) to change the basal transcription level dictated by the promoter.

Preferably, the isolated genetic material is introduced into the cell genome immediately downstream from the promoter so that the promoter and coding sequence are operatively linked so as to permit transcription of the coding sequence. Preferred viral expression vectors include an exogenous promoter element to control transcription of the inserted interferon gene. Such exogenous promoters include both constitutive and inducible promoters.

Naturally-occurring constitutive promoters control the expression of proteins that regulate essential cell functions. As a result, a gene under the control of a constitutive promoter is expressed under all conditions of cell growth. Exemplary constitutive promoters include the promoters for the following genes which encode certain constitutive or "housekeeping" functions: hypoxanthine phosphoribosyl transferase (HPRT), dihydrofolate reductase (DHFR) (Scharfmann et al., *Proc. Natl. Acad. Sci. USA* 88: 4626-4630 (1991)), adenosine deaminase, phosphoglycerol kinase (PGK), pyruvate kinase, phosphoglycerol mutase, the β-actin promoter (Lai et al., *Proc. Natl. Acad. Sci. USA* 86: 10006-10010 (1989)), and other constitutive promoters known to those of skill in the art.

In addition, many viral promoters function constitutively in eucaryotic cells. These include: the early and late promoters of SV40 (See Bernoist and Chambon, *Nature,* 290: 304 (1981)); the long terminal repeats (LTRs) of Moloney Leukemia Virus and other retroviruses (See Weiss et al., RNA Tumor Viruses, Cold Spring Harbor Laboratory, Cold Spring Harbor, N.Y. (1985)); the thymidine-kinase promoter of Herpes Simplex Virus (HSV) (See Wagner et al., *Proc. Nat. Acad. Sci. USA,* 78: 1441 (1981)); the cytomegalovirus immediate-early (IE1) promoter (See Karasuyama et al., *J. Exp. Med.,* 169: 13 (1989); the promoter of the Rous sarcoma virus (RSV) (Yamamoto et al., *Cell,* 22:787 (1980)); the adenovirus major late promoter (Yamada et al., *Proc. Nat. Acad. Sci. USA,* 82: 3567 (1985)), among many others. Accordingly, any of the above-referenced constitutive promoters can be used to control transcription of a gene insert. (See also Section B).

If delivery of the interferon gene is to specific tissues, it may be desirable to target the expression of this gene. For instance, there are many promoters described in the literature which are only expressed in certain tissues. Examples include liver-specific promoters of hepatitis B virus (Sandig et al., *Gene Therapy* 3: 1002-1009 (1996) and the albumin gene (Pinkert et al., *Genes and Development,* 1: 268-276 (1987); see also Guo et al., *Gene Therapy,* 3: 802-810 (1996) for other liver-specific promoter. Moreover, there are many promoters described in the literature which are only expressed in specific tumors. Examples include the PSA promoter (prostate carcinoma), carcinoembryonic antigen promoter (colon and lung carcinoma), β-casein promoter (mammary carcinoma), tyrosinase promoter (melanoma), calcineurin Aα promoter (glioma, neuroblastoma), c-sis promoter (osteosarcoma) and the α-fetoprotein promoter (hepatoma).

Genes that are under the control of inducible promoters are expressed only, or to a greater degree, in the presence of an inducing agent, (e.g., transcription under control of the metallothionein promoter is greatly increased in presence of certain metal ions). See also the glucocorticoid-inducible promoter present in the mouse mammary tumor virus long terminal repeat (MMTV LTR) (Klessig et al., *Mol. Cell. Biol.,* 4: 1354 (1984)). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene.

Thus, by selecting the appropriate promoter (constitutive versus inducible; strong versus weak), it is possible to control both the existence and level of expression of a interferon in the genetically modified cell. If the gene encoding the interferon is under the control of an inducible promoter, delivery of the interferon in situ is triggered by exposing the genetically modified cell in situ to conditions permitting transcription of the interferon, e.g., by injection of specific inducers of the inducible promoters which control transcription of the agent. For example, in situ expression by genetically modified cells of interferon protein encoded by an interferon gene under the control of the metallothionein promoter is enhanced by contacting the genetically modified cells with a solution containing the appropriate (i.e., inducing) metal ions in situ.

Recently, very sophisticated systems have been developed which allow precise regulation of gene expression by exogenously administered small molecules. These include, the FK506/Rapamycin system (Rivera et al., *Nature Medicine* 2(9): 1028-1032, 1996); the tetracycline system (Gossen et al., *Science* 268: 1766-1768,1995), the ecdysone system (No et al., *Proc. Nat. Acad. Sci., USA* 93: 3346-3351,1996) and the progesterone system (Wang et al., *Nature Biotechnology* 15: 239-243,1997).

Accordingly, the amount of interferon that is delivered in situ is regulated by controlling such factors as: (1) the nature of the promoter used to direct transcription of the inserted gene, (i.e., whether the promoter is constitutive or inducible, strong or weak or tissue specific); (2) the number of copies of the exogenous gene that are inserted into the cell; (3) the number of transduced/transfected cells that are administered (e.g., implanted) to the patient; (4) the size of an implant (e.g., graft or encapsulated expression system) in ex vivo methods; (5) the number of implants in ex vivo methods; (6) the number of cells transduced/transfected by in vivo administration; (7) the length of time the transduced/transfected cells or implants are left in place in both ex vivo and in vivo methods; and (8) the production rate of the interferon by the genetically modified cell.

Selection and optimization of these factors for delivery of a therapeutically effective dose of a particular interferon is deemed to be within the scope of one of ordinary skill in the art without undue experimentation, taking into account the above-disclosed factors and the clinical profile of the patient.

Because the protein expressed by our gene therapy methods is a secreted protein, surrounding cells that do not contain the gene therapy vector are still affected (see Examples). As a result, the present methods typically do not require use of a selectable gene. Nevertheless, in addition to at least one promoter and at least one isolated polynucleotide encoding the interferon, the expression vector may optionally include a selection gene, for example, a neomycin resistance gene, for facilitating selection of cells that have been transfected or transduced with the expression vector. Alternatively, the cells are transfected with two or more expression vectors, at least one vector containing the gene(s) encoding the interferon(s), the other vector containing a selection gene. The selection of a suitable promoter, enhancer, selection gene and/or signal sequence (described below) is deemed to be within the scope of one of ordinary skill in the art without undue experimentation.

IV. Methods of Preparing Specific Gene Therapy Vectors

Any of the methods known in the art for the insertion of polynucleotide sequences into a vector may be used. See, for example, Sambrook et al., *Molecular Cloning: A Laboratory Manual*, Cold Spring Harbor Laboratory, Cold Spring Harbor, N.Y. (1989) and Ausubel et al., *Current Protocols in Molecular Biology*, J. Wiley & Sons, N.Y. (1992). Conventional vectors consist of appropriate transcriptional/translational control signals operatively linked to the polynucleotide sequence for a particular interferon. Promoters/enhancers may also be used to control expression of interferons. (See Section III)

Expression vectors compatible with mammalian host cells for use in gene therapy of tumor cells include, for example, plasmids; avian, murine and human retroviral vectors; adenovirus vectors; herpes viral vectors; parvoviruses; and non-replicative pox viruses. In particular, replication-defective recombinant viruses can be generated in packaging cell lines that produce only replication-defective viruses. See *Current Protocols in Molecular Biology*: Sections 9.10-9.14 (Ausubel et al., eds.), Greene Publishing Associcates, 1989.

Specific viral vectors for use in gene transfer systems are now well established. See for example: Madzak et al., *J. Gen. Virol.*, 73: 1533-36 (1992) (papovavirus SV40); Berkner et al., *Curr. Top. Microbiol. Immunol.*, 158: 39-61 (1992) (adenovirus); Moss et al., *Curr. Top. Microbiol. Immunol.*, 158: 25-38 (1992) (vaccinia virus); Muzyczka, *Curr. Top. Microbiol. Immunol.*, 158: 97-123 (1992) (adeno-associated virus); Margulskee, *Curt. Top. Microbiol. Immunol.*, 158: 67-93 (1992) (herpes simplex virus (HSV) and Epstein-Barr virus (HBV)); Miller, *Curr. Top. Microbiol. Immunol.*, 158:1-24 (1992) (retrovirus); Brandyopadhyay et at., *Mol. Cell. Biol.*, 4: 749-754 (1984) (retrovirus); Miller et al., *Nature*, 357: 455-460 (1992) (retrovirus); Anderson, *Science*, 256: 808-813 (1992) (retrovirus).

Preferred vectors are DNA viruses that include adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al., *Gene Therapy* 1: 367-384,1994; U.S. Pat. Nos. 4,797,368 and 5,399,346 and discussion below.

The choice of a particular vector system for transferring, for instance, a interferon sequence will depend on a variety of factors. One important factor is the nature of the target cell population. Although retroviral vectors have been extensively studied and used in a number of gene therapy applications, they are generally unsuited for infecting cells that are not dividing but may be useful in cancer therapy since they only integrate and express their genes in replicating cells. They are useful for ex vivo approaches and are attractive in this regard due to their stable integration into the target cell genome.

Adenoviruses are eukaryotic DNA viruses that can be modified to efficiently deliver a therapeutic or reporter transgene to a variety of cell types. The general adenoviruses types 2 and 5 (Ad2 and Ad5, respectively), which cause respiratory disease in humans, are currently being developed for gene therapy of Duchenne Muscular Dystrophy (DMD) and Cystic Fibrosis (CF). Both Ad2 and Ad5 belong to a subclass of adenovirus that are not associated with human malignancies. Adenovirus vectors are capable of providing extremely high levels of transgene delivery to virtually all cell types, regardless of the mitotic state. High titers ($10^{11}$ plaque forming units/ml) of recombinant virus can be easily generated in 293 cells (an adenovirus-transformed, complementation human embryonic kidney cell line: ATCC CRL1573) and cryo-stored for extended periods without appreciable losses. The efficiency of this system in delivering a therapeutic transgene in vivo that complements a genetic imbalance has been demonstrated in animal models of various disorders. See Y. Watanabe, *Atherosclerosis*, 36: 261-268 (1986); K Tanzawa et al, *FEBS letters,* 118(1):81-84 (1980); J. L. Golasten et al, *New Engl. J. Med.,* 309

(11983): 288-296 (1983); S. Ishibashi et al, *J. Clin. Invest.,* 92: 883-893 (1993); and S. Ishibashi et al, *J. Clin. Invest.,* 93: 1889-1893 (1994). Indeed, recombinant replication defective adenovirus encoding a cDNA for the cystic fibrosis transmembrane regulator (CFTR) has been approved for use in several human CF clinical trials. See, e.g., J. Wilson, *Nature,* 365: 691-692 (Oct., 21, 1993). Further support of the safety of recombinant adenoviruses for gene therapy is the extensive experience of live adenovirus vaccines in human populations.

Human adenoviruses are comprised of a linear, approximately 36 kb double-stranded DNA genome, which is divided into 100 map units (m.u.), each of which is 360 bp in length. The DNA contains short inverted terminal repeats (ITR) at each end of the genome that are required for viral DNA replication. The gene products are organized into early (E1 through E4) and late (L1 through L5) regions, based on expression before or after the initiation of viral DNA synthesis. See, e.g., Horwitz, Virology, 2d edit., ed. B. N. Fields, Raven Press Ltd., New York (1990).

The adenovirus genome undergoes a highly regulated program during its normal viral life cycle. See Y. Yang et, al *Proc. Natl. Acad. Sci. U.S.A,* 91: 4407-4411(1994). Virions are internalized by cells, enter the endosome, and from there the virus enters the cytoplasm and begins to lose its protein coat. The virion DNA migrates to the nucleus, where it retains its extrachromosomal linear structure rather than integrating into the chromosome. The immediate early genes, E1a and E1b, are expressed in the nucleus. These early gene products regulate adenoviral transcription and are required for viral replication and expression of a variety of host genes (which prime the cell for virus production), and are central to the cascade activation of delayed early genes (e.g. E2, E3, and E4) followed by late genes (e.g. L1-L5).

The first-generation recombinant, replication-deficient adenoviruses which have been developed for gene therapy contain deletions of the entire E1a and part of the E1b regions. This replication-defective virus is grown in 293 cells which contain a functional adenovirus E1 region which provides in trans E1 proteins, thereby allowing replication of E1-deleted adenovirus. The resulting virus is capable of infecting many cell types and can express the introduced gene (providing it carries a promoter), but cannot replicate in a cell that does not carry the E1 region DNA. Recombinant adenoviruses have the advantage that they have a broad host range, can infect quiescent or terminally differentiated cells such as neurons, and appear essentially non-oncogenic. Adenoviruses do not appear to integrate into the host genome. Because they exist extrachromasomally, the risk of insertional mutagenesis is greatly reduced. Recombinant adenoviruses produce very high titers, the viral particles are moderately stable, expression levels are high, and a wide range of cells can be infected.

Adeno-associated viruses (AAV) have also been employed as vectors for somatic gene therapy. AAV is a small, single-stranded (ss) DNA virus with a simple genomic organization (4.7 kb) that makes it an ideal substrate for genetic engineering. Two open reading frames encode a series of rep and cap polypeptides. Rep polypeptides (rep78, rep68, rep 62 and rep 40) are involved in replication, rescue and integration of the AAV genome. The cap proteins (VP 1, VP2 and VP3) form the virion capsid. Flanking the rep and cap open reading frames at the 5' and 3' ends are 145 bp inverted terminal repeats (ITRs), the first 125 bp of which are capable of forming Y- or T-shaped duplex structures. Of importance for the development of AAV vectors, the entire rep and cap domains can be excised and replaced with a therapeutic or reporter transgene. See B. J. Carter, in Handbook of Parvoviruses, ed., P. Tijsser, CRC Press, pp. 155-168 (1990). It has been shown that the ITRs represent the minimal sequence required for replication, rescue, packaging, and integration of the AAV genome.

The AAV life cycle is biphasic, composed of both latent and lytic episodes. During a latent infection, AAV virions enter a cell as an encapsidated ssDNA, and shortly thereafter are delivered to the nucleus where the AAV DNA stably integrates into a host chromosome without the apparent need for host cell division. In the absence of a helper virus, the integrated AAV genome remains latent but capable of being activated and rescued. The lytic phase of the life cycle begins when a cell harboring an AAV provirus is challenged with a secondary infection by a herpesvirus or adenovirus which encodes helper functions that are required by AAV to aid in its excision from host chromatin (B. J. Carter, supra). The infecting parental single-stranded (ss) DNA is expanded to duplex replicating form (RF) DNAs in a rep dependent manner. The rescued AAV genomes are packaged into preformed protein capsids (icosahedral symmetry approximately 20 nm in diameter) and released as infectious virions that have packaged either + or − ssDNA genomes following cell lysis.

AAV have significant potential in gene therapy. The viral particles are very stable and recombinant AAVs (rAAV) have "drug-like" characteristics in that rAAV can be purified by pelleting or by CsCl gradient banding. They are heat stable and can be lyophilized to a powder and rehydrated to full activity. Their DNA stably integrates into host chromosomes so expression is long-term. Their host range is broad and AAV causes no known disease so that the recombinant vectors are non-toxic.

High level gene expression from AAV in mice was shown to persist for at least 1.5 years. See Xiao, Li and Samuiski (1996) *Journal of Virology* 70, 8089-8108. Since there was no evidence of viral toxicity or a cellular host immune response, these limitations of viral gene therapy have been overcome.

Kaplitt, Leone, Samulski, Xiao, Pfaff, O'Malley and During (1994) *Nature Genetics* 8, 148-153 described long-term (up to 4 months) expression of tyrosine hydroxylase in the rat brain following direct intracranial injection using an AAV vector. This is a potential therapy for Parkinson's Disease in humans. Expression was highly efficient and the virus was safe and stable.

Fisher et al. (*Nature Medicine* (1997) 3, 306-312) reported stable gene expression in mice following injection into muscle of AAV. Again, the virus was safe. No cellular or humoral immune response was detected against the virus or the foreign gene product.

Kessler et al. (*Proc. Natl. Acad. Sci. USA* (1996) 93, 14082-14087) showed high-level expression of the erythropoietin (Epo) gene following intramuscular injection of AAV in mice. Epo protein was demonstrated to be present in circulation and an increase in the red blood cell count was reported, indicative of therapeutic potential. Other work by this group has used AAV expressing the HSV tk gene as a treatment for cancer. High level gene expression in solid tumors has been described.

Recently, recombinant baculovirus, primarily derived from the baculovirus *Autographa califomica* multiple nuclear polyhedrosis virus (AcMNPV), has been shown to be capable of transducing mammalian cells in vitro. (See Hofmann, C., Sandig, V., Jennings, G., Rudolph, M., Schlag, P., and Strauss, M. (1995), "Efficient gene transfer into human hepatocytes by baculovirus vectors", *Proc. Natl.*

Acad. Sci. USA 92, 10099-10103; Boyce, F. M. and Bucher, N. L. R. (1996) "Baculovirus-mediated gene transfer into mammalian cells", *Proc. Natl. Acad. Sci. USA* 93, 2348-2352).

Recombinant baculovirus has several potential advantages for gene therapy. These include a very large DNA insert capacity, a lack of a preexisting immune response in humans, lack of replication in mammals, lack of toxicity in mammals, lack of expression of viral genes in mammalian cells due to the insect-specificity of the baculovirus transcriptional promoters, and, potentially, a lack of a cytotoxic T lymphocyte response directed against these viral proteins IV. Testing for Efficacy/Identification of Interferons Interferon polynucleotides are administered to a cell via an expression vector. Generally, one tests the efficacy of a given gene therapy vector on a particular cellular condition and metabolism by assaying for: (i) alterations in cellular morphology; (ii) inhibition of cell proliferation; and (iii) antiviral activities.

The selection and optimization of a particular expression vector for expressing a specific interferon gene product in an isolated cell is accomplished by obtaining the interferon gene, preferably with one or more appropriate control regions (e.g., promoter); preparing a vector construct comprising the vector into which is inserted the interferon gene; transfecting or transducing cultured cells in vitro with the vector construct; and determining whether the interferon gene product is present in the cultured cells.

The effect of transfection with polynucleotides encoding interferons may be tested in vitro using any one of a number of readily available human tumor cell lines. Such cell line include a human bladder carcinoma cell line, 5637 (ATCC HTB9), a human breast carcinoma cell line, MDA-MB468 (ATCC HTB132); a human prostate carcinoma cell line, DU145 (ATCC HTB81); a human osteosarcoma cell line, SAOS2 (ATCC HTB85); a human fibrosarcoma metastatic to lung cancer cell line, Hs913T (ATCC HTB152); a human cervical carcinoma cell line, HeLa (ATCC ECL 2). Each of these cell lines may be transfected with the appropriate polynucleotides encoding interferons and the effect of transfection on cell growth and cellular morphology may be tested using procedures known in the art such as the Trypan blue exclusion assay to measure cell viability, cell counting to measure propagation over time and tritiated-thymidine incorporation to measure DNA replication.

The effect of a secreted protein on surrounding cells that do not contain a viral vector with the appropriate polynucleotides encoding the protein, may be easily tested using the methods described in Example 3.

Once introduced into a target cell, interferon sequences can be identified by conventional methods such as nucleic acid hybridization using probes comprising sequences that are homologous/complementary to the inserted mutant interferon sequences. Interferon transcription can be measured by reverse transcriptase polymerase chain reaction. Alternatively, interferon protein is measured in the cell-conditioned medium by conventional antiviral assay or ELISA assay. In another approach, the sequence(s) may be identified by the presence or absence of a "marker" gene function (e.g, thymidine kinase activity, antibiotic resistance, and the like) caused by introduction of the expression vector into the target cell. For instance, if a polynucleotide encoding interferon-beta 1a is inserted into a vector having a dominant selectable marker gene such as a neomycin phosphotransferase gene under separate control of an SV40 early promoter, the sequence can be identified by the presence of the marker gene function (Geneticin resistance). Other methods of detecting the appropriate vector will be readily available to persons having ordinary skill in the art.

V. Utilities

A. Interferons and Infectious Diseases

Interferons have been used in the treatment of bacterial, fungal and viral infections. Influenza and vesicular stomatitis virus (VSV) are particularly sensitive to inhibition by interferons and are often used in assays to measure interferon activity and in research exploring the mechanism of interferon antiviral activity. Other viruses which are human pathogens and appear to be sensitive to interferons include hepatitis B virus (HBV), hepatitis C virus (HCV), hepatitis D virus, human papillomavirus, herpes simplex virus, herpes zoster virus, cytomegalovirus (CMV), rhinovirus and encephalomyocarditis virus.

Among the more attractive viral disease targets is hepatitis. Viral hepatitis, a liver disease caused by multiple viruses, is a major world-wide health problem. Five distinct human hepatitis viruses have been isolated and cloned. These are hepatitis A, B, C, D and E. Some cases of acute and chronic viral hepatitis appear to be associated with hepatitis virus(es) other than those already characterized, such as the newly discovered hepatitis G virus. Viruses with the highest prevalence are A, B and C. In addition to causing acute and chronic liver injury and inflammation, HBV and HCV infection can lead to hepatocellular carcinoma. Interferons have demonstrated some level of efficacy in vivo against HBV and HCV, as well as hepatitis D and hepatitis A in cell culture.

Viral hepatitis could be treated by introduction of the interferon gene. The preferred target for delivery of this gene are the hepatocytes in the liver. Although ex vivo therapy (e.g., explanting liver cells followed by introduction of the polynucleotide expressing interferon and then transplantation back into the patient) is possible, gene delivery in vivo is particularly preferable. Surgery is performed to inject the gene into the portal vein of the liver or the gene is infused through a catheter into the hepatic artery. Ideally, less invasive practices such as intravenous injection are used.

The interferon gene is placed under the control of a transcriptional promoter in a suitable expression vector. The transcriptional promoter can be cellular or viral (CMV, SV40, RSV, etc.) in origin. If liver-specific gene expression is desired, a hepatocyte-specific cellular promoter such as the albumin enhancer/promoter, the α1-antitrypsin promoter or an HBV enhancer/promoter is preferred. There are many liver-specific promoters described in the literature (See supra).

It is also possible to design a vector in which the interferon gene is only expressed in hepatitis-infected cells. For instance, expression of the interferon gene could be induced by the HBV transcription factor HBx which will only be present in HBV-infected hepatocytes. In addition, a "carrier" system may be used. This could be a non-viral delivery system such as cationic liposomes or protein:DNA conjugates (conjugates of DNA with asialoglycoproteins can be delivered preferentially to the liver via binding to the asialoglycoprotein receptor on hepatocytes).

However, to date, the most efficient gene delivery systems are viral in origin. Recombinant retroviruses have been used to deliver genes to human hepatocytes ex vivo. Animal models indicate that recombinant adenovirus can very efficiently localize to the liver following intravenous in vivo administration. Approximately 98% of adenovirus injected intravenously localizes to the liver.

It appears that recombinant adeno-associated virus (rAAV) can also infect liver after in vivo administration. Other types of viruses such as alpha viruses, lentiviruses or other mammalian viruses could be used. Recently, a non-mammalian virus, the insect-specific baculovirus has been shown to be able to deliver and express genes efficiently in hepatocytes (Hofman et al., 1995; Boyce and Bucher, 1996, supra).

By way of example, recombinant adenoviruses can be utilized to deliver the interferon gene in vivo. Replication-defective adenoviruses have been constructed by multiple groups. The first generation of such viruses are defective due to the deletion of the E1 region. This defect is complemented in the 293 cell line which expresses the adenovirus E1 region. It is preferable to use a recombinant adenovirus which has been more extensively crippled by deletion of the E1, E2a and/or E4 genes. All of these deleted functions can be expressed in the packaging cell line. The interferon gene is placed downstream of any of a large number of promoters (for example: the CMV immediate early promoter, the RSV LTR, the cellular actin promoter, the albumin enhancer/promoter or other liver-specific promoter). This gene cassette is placed into a recombinant adenovirus vector in place of one of the deleted genes, such as E1 to create the adenovirus transfer vector.

Recombinant adenoviruses having the interferon gene are generated via direct ligation or homologous recombination following transfection into packaging cells by standard methods. A recombinant virus stock having the interferon gene is plaque purified multiple times then expanded by large-scale production in packaging cells. Virus can be purified by CsCl banding, column chromatography or other methods and then titered on the packaging cells. Methods for generating adenoviruses defective in E1 and E2a (Engelhardt et al., *Proc. Nat. Acad. Sci. USA,* 91: 6196-6200, 1994) and adenoviruses defective in E1 and E4 (Gao et al., *J. Virology,* 70: 8934-8943, 1996) have been described in detail. Methods for generating adenoviruses defective in E1 can be found in Graham, F. L. and L. Prevec, "Methods for Construction of Adenovirus Vectors", Mol. Biotech, 3: 207-220 (1995).

Various doses of viruses would be tested in trials. The dose of virus would likely start at $10^7$ plaque-forming units (pfu) and go up to $10^{12}$ pfu. If necessary, the virus could be administered repeatedly (once every one to six months, for instance). A humoral immune response resulting from repeated viral administration may limit the effectiveness of repeat administration. In this case, a immunosuppressive agent could be administered along with the virus such as cyclosporine or antibody directed against CD40 ligand.

The effect of interferon gene therapy against viral hepatitis can be tested in animal models (See Section C). For instance, in the case of hepatitis B virus, many models are available. These include woodchuck, duck, tree shrew, rat and mouse. Included among the mouse HBV models are mice that are transgenic for HBV and stably replicate HBV DNA in their livers leading to the steady production of HBV virus in circulation. For HCV, a chimpanzee model is available. Adenovirus having an interferon gene could be directly administered into liver or be given by intravenous injection. Efficacy would be determined by monitoring viral DNA replication, viral particles in circulation, liver enzymes (ALTs), liver pathology and inflammation.

B. Cancer

Interferon proteins have been shown to possess anti-oncogenic activity in many settings. For reviews, see Wadler and Schwartz, *Cancer Research* 50: 3473-3486, 1990; Martin-Odegard, *DN&P,* 4: 116-117,1991; and Spiegel, *Seminars in Oncology* 15 (5): 41-45, 1988. Treatment with interferon-alpha and interferon-beta have shown some efficacy against several cancers. Gene therapy could be done alone or in conjunction with conventional surgery, radiation or chemotherapy. The following list of cancers amenable to gene therapy is only a partial one and it is likely that interferon gene therapy could be effective in a number of disease settings which are not included in this list.

Malignant gliomas account for 60-80% of all primary brain tumors in adults. Human glioma cells can be implanted intracerebrally into immuno-deficient (nude) mice to provide a glioma model. Interferon-beta protein treatment has been shown to increase survival in these mice. A problem with some of the interferon-beta protein trials in glioma has been the high toxicity following parenteral administration (intravenous or, intramuscular) of interferon-beta. Localized delivery of the interferon-beta gene into the brain, perhaps at the time of surgery, could result in long-term interferon-beta production in the brain without the side-effects seen following systemic protein administration.

Melanoma is an excellent target for interferon gene therapy. The prognosis for metastatic malignant melanoma is poor. The incidence of disease is increasing dramatically and conventional chemotherapies are ineffective. Melanoma appears to be an immunogenic tumor type, in that the patient response may depend on the host immune response. Both the anti-proliferative and immunomodulatory activities of interferon-beta could be effective in this setting. We have seen that interferon-beta protein has direct anti-proliferative effects on cultured malignant melanoma cells.

Hemangioma is a proliferation of capillary endothelium resulting in the accumulation of mast cells, fibroblasts and macrophages, and leads to tissue damage. Although usually harmless, hemangiomas can endanger vital organs and cause fatalities. Interferon-alpha protein was shown to induce early regression of steroid-resistant hemangiomas in infants (Martin-Odegard, supra).

Interferon proteins have been shown to be effective in the treatment of leukemias, lymphomas and myelomas. The efficacy shown in these diseases is contrary to the general finding that, although efficacy of interferon proteins in in vitro cancer treatment is well-characterized, in vivo efficacy is far less common. Nevertheless, interferon-alpha is efficacious against hairy cell leukemia, chronic myeloid leukemia, cutaneous T cell lymphomas, Hodgkin's lymphoma and multiple myeloma in human clinical trials. Interferon-beta protein inhibits the growth of renal cell carcinoma cells in culture. IFN-α has already been approved for use in the treatment of renal cell carcinoma.

Colorectal cancer is a major cause of cancer-related deaths in the U.S. There are potent anti-proliferative effects by IFN-α, IFN-β and IFN-γ proteins on cultured human colon carcinoma cells. Colon carcinoma often generates metastases in the liver with dire consequences. Adenovirus or other liver-tropic delivery systems could be used to deliver the interferon gene to the liver for treatment of these metastases. *Hepatocellular carcinoma* is an attractive target due to the high efficiency of liver delivery by adenovirus. It has been observed that IFN-β protein significantly inhibits the proliferation of human hepatoma cells in culture.

Interferon proteins have shown efficacy in the treatment of inoperable non-small cell lung carcinoma in some clinical trials, but not in others. Two human lung cancer cell lines are found to be sensitive to growth inhibition by interferon-beta protein (beta was more effective than alpha). In one clinical trial, significant interferon-related toxicity was observed after intravenous interferon administration. Local delivery of the interferon-beta gene to the lung (perhaps by aerosol delivery of a recombinant adenovirus vector) could be efficacious without the toxicity observed following systemic protein delivery. In vitro, the inhibition in proliferation of small-cell lung carcinoma cells using interferon-beta protein has been observed.

Interferon-alpha protein inhibits the growth of breast cancer xenografts in nude mice. Interferon-beta may be efficacious against breast cancer due not only to its anti-proliferative effects but also due to its induction of estrogen receptors and progesterone receptors in vivo to sensitize breast carcinomas to the anti-estrogen tamoxifen. I present data from experiments using IFN-β gene therapy in a mouse model of human breast carcinoma (See Examples 3 and 4).

Ovarian cancer is a possible disease target. Interferon-beta protein appears to be less active than interferon-alpha in inhibition of proliferation of cultured ovarian cancer cells. Therapy, in this case, could be done by installation of the gene therapy vector into the peritoneum as this type of tumor tends to fill the peritoneal cavity.

In summary, interferon proteins have demonstrated anti-oncogenic properties in a number of settings although clinical results using interferon protein are not uniformly positive. IFN-α and IFN-β proteins have been tested in conjunction with conventional chemotherapeutics and have shown synergy with these drugs in many indications including cervical cancer cells, laryngeal carcinoma cells, leukemia cells, renal cell carcinomas, colon adenocarcinoma and myeloma. It is also believed that interferons possess anti-angiogenesis activity. There is an inverse correlation between local IFN-β levels and angiogenic capability. Some data indicate that a sustained level of IFN-β protein is necessary for the inhibition of angiogenesis. In that case, interferon gene therapy would be preferable to protein therapy in which the high levels of interferon protein fall off to low or undetectable levels quite rapidly.

C. Animal Gene Therapy Models

Persons having ordinary skill in the art will be aware of the many animal models that are available to test ex vivo and in vivo gene therapy. The most commonly used rodent cancer model is the human tumor xenograft model in nude (nu/nu) mice. The human cancer cells are propagated in culture and transfected or infected with a gene encoding interferon operably linked to the appropriate expression control sequences. These cells are then injected into a nude mouse. Typically, the tumor cells are injected subcutaneously into the back of the mouse leading to the formation of a solid tumor mass (See Example 1). Alternatively, the tumor cells could be injected orthotopically into the organ in which they would naturally appear (lung cancer cells would be injected into the lung; colon carcinoma cells into the colon, etc.). Tumor growth can then be followed by measuring the diameter of the tumor mass over time (See Example 2).

Okada et al. (1996) *Gene Therapy* 3, 957-964 formed experimental gliomas in mice by direct intracranial stereotactic injection of human glioma cells into the brain. After detectable tumors formed, an AAV vector expressing the herpes simplex virus thymidine kinase gene (HSV tk) was injected directly into the same site. The HSV tk enzyme converts the non-toxic nucleoside analogue gancyclovir (GCV) into a toxic metabolite. After gene therapy, GCV was administered intraperitoneally. Mice which received AAV-tk plus GCV, but not control AAV or AAV-tk without GCV, displayed a dramatic reduction in tumor size. This therapy appeared to be safe and effective.

Recombinant adenoviruses (AdV) have also been used in the treatment of solid tumors in animal models and in early human clinical trials. Many of these studies used similar nude mouse/human xenograft models. Some examples of these modeling experiments are listed below. Clayman et al. (1995) *Cancer Research* 55, 1-6 set up a model of human squamous cell carcinoma of the head and neck in nude mice. They found that adenovirus expressing wild type p53 prevented formation of these tumors.

Hirschowitz et al. (1995) *Human Gene Therapy* 6, 1055-1063 introduced human colon carcinoma cells into nude mice. After tumors are established, they injected these tumors directly with adenovirus expressing the *E. coli* cytosine deaminase gene (CD) then administered 5-fluorocytosine (5FC) systemically (CD plus 5FC is a enzyme/prodrug combination similar to tk plus GCV). They observed a 4 to 5-fold reduction in tumor size.

Zhang et al. (1996) *Proc. Natl. Acad. Sci USA* 93, 4513-4518 formed human breast tumors in nude mice. These tumors are injected directly with adenovirus expressing interferon-alpha. They observed tumor regression in 100% of the animals.

Ko et al. (1996) *Human Gene Therapy* 7, 1683-1691 formed human prostate tumors in nude mice and found that direct intratumoral injection of adenovirus expressing wild type p53 inhibited tumor growth. All treated mice remained tumor free for at least 12 weeks after the cessation of treatment.

Bischoff et al. (1996) *Science* 274, 373-376 formed human cervical carcinoma and glioblastoma tumors in nude mice. They treated these mice with an adenovirus which had a deletion of the E1B gene. In the absence of E1B, adenovirus selectively kills p53-deficient tumor cells. When injected directly into the tumors, this adenovirus caused tumor regression in 60% of the animals.

Ohwada et al. (1996) *Human Gene Therapy* 7, 1567-1576 injected human colon carcinoma cells into the liver of nude mice to mimic liver metastases of colon cancer. They then injected adenovirus expressing CD into the liver near the tumor. Systemic 5FC treatment suppressed tumor growth in these animals.

Cancer models also can be set up in immunocompetent mice and rats. These tumors can be established from syngeneic rodent tumor cells which are injected into the mice. Alternatively, the tumors can derive from endogenous cells. In these cases, the endogenous tumors could be due to treatment of the animal with a carcinogen or, alternatively, can form spontaneously due to the genetic background of the mouse (deficient in p53, for instance). Some examples follow.

Elshami et al. (1996) *Human Gene Therapy* 7, 141-148 treated endogenous mesothelioma in immunocompetent rats with adenovirus expressing the tk gene. The virus was injected into the pleural space, and then GCV was administered systemically. They showed a dramatic decrease in tumor weight and an increase in survival time.

Eastham et al. (1996) *Human Gene Therapy* 7, 515-523 implanted syngeneic mouse prostate tumor cell lines subcutaneously into immunocompetent mice. They directly injected adenovirus-tk into the tumor and treated with GCV systemically. The authors reported decreased tumor size and prolonged life.

Bramson et al. (1996) *Human Gene Therapy* 7, 1995-2002 injected adenovirus expressing the cytokine IL-12 directly into endogenous mouse breast tumors. They found that 75% of the mice had regression of the tumors, and 33% remained tumor free after an extended period of time.

Riley et al. (1996) *Nature Medicine* 2, 1336-1341 injected adenovirus expressing the retinoblastoma gene directly into pituitary melanotroph tumors which arose spontaneously in Rb+/− mice. They found decreased tumor cell proliferation, decreased tumor growth and prolonged life span in treated animals.

Retrovirus vectors are the first vectors used in human gene therapy clinical trials. One report which is relevant to the present patent application is that of Roth et al. (1996) *Nature Medicine* 2, 985-991. They generated recombinant retrovirus which expressed the wild type p53 gene. This virus was introduced into nine human patients having non-small cell lung carcinoma by direct intratumoral injection using a needle inserted in a bronchoscope. Of the nine patients, three displayed tumor regression while three other patients showed stabilization of tumor growth.

D. Other Embodiments

The genetically modified cells are administered by, for example, intraperitoneal injection or by implanting the cells or a graft or capsule containing the cells in a cell-compatible site of the recipient. As used herein, "cell-compatible site" refers to a structure, cavity or fluid of the recipient into which the genetically modified cell(s), cell graft, or encapsulated cell expression system can be implanted, without triggering adverse physiological consequences. Representative cell-compatible sites include, for example, the peritoneal, pleural and pericardial cavities as well as a solid tumor from which the cells were derived or the organ from which the tumor was removed.

The genetically modified cells are implanted in a cell-compatible site, alone or in combination with other genetically modified cells. Thus, the instant invention embraces a method for modifying the system of a recipient by using a mixture of genetically modified cells, such that a first modified cell expresses a first interferon and a second modified cell expresses a second interferon or other secreted protein. Other genetically modified cell types (e.g., hepatocytes, smooth muscle cells, fibroblasts, glial cells, endothelial cells or keratinocytes) can be added, together with the genetically altered cells, to produce expression of a complex set of introduced genes. Moreover, more than one recombinant gene can be introduced into each genetically modified cell on the same or different vectors, thereby allowing the expression of multiple interferons by a single cell.

The instant invention further embraces a cell graft. The graft comprises a plurality of the above-described genetically modified cells attached to a support that is suitable for implantation into a mammalian recipient. The support can be formed of a natural or synthetic material. In another embodiment, the graft comprises a patch of peritoneum. Accordingly to this embodiment, the support is the naturally-occurring matrix that holds the plurality of genetically modified cells together. Alternatively, the graft comprises a plurality of the above-described cells attached to a substitute for the naturally occurring matrix (e.g., Gelfoam (Upjohn, Kalamazoo, Mich.), Dacron, Cortex®).

According to another aspect of the invention, an encapsulated cell expression system is provided. The encapsulated system includes a capsule suitable for implantation into a mammalian recipient and a plurality of the above-described genetically modified mesothelail cells contained therein. The capsule can be formed of a synthetic or naturally-occurring material. The formulation of such capsules is known to one of ordinary skill in the art. In contrast to the cells which are directly implanted into the mammalian recipient (i.e., implanted in a manner such that the genetically modified cells are in direct physical contact with the cell-compatible site), the encapsulated cells remain isolated (i.e., not in direct physical contact with the site) following implantation. Thus, the encapsulated system is not limited to a capsule including genetically-modified non-immortalize cells, but may contain genetically modified immortalized cells.

VI. Formulations.

In a preferred embodiment, the preparation of genetically modified cells contains an amount of cells sufficient to deliver a therapeutically effective dose of the interferon to the recipient in situ. The determination of a therapeutically effective dose of a specific interferon for a known condition is within the scope of one of ordinary skill in the art without the need for undue experimentation. Thus, in determining the effective dose, one of ordinary skill would consider the condition of the patient, the severity of the condition, as well as the results of clinical studies of the specific interferon being administered.

If the gene or the genetically modified cells are not already present in a pharmaceutically acceptable carrier they are placed in such a carrier prior to administration to the recipient. Such pharmaceutically acceptable carriers include, for example, isotonic saline and other buffers as appropriate to the patient and therapy.

The term "pharmaceutically acceptable carrier" means one or more ingredients, natural or synthetic, with which the isolated polynucleotide encoding interferon is combined to facilitate its application. A suitable carrier includes sterile saline although other aqueous and non-aqueous isotonic sterile solutions and sterile suspensions known to be pharmaceutically acceptable are known to those of ordinary skill in the art. In this regard, the term "carrier" encompasses any plasmid and viral expression vectors. An "effective amount" refers to that amount which is capable of ameliorating or delaying progression of the diseased, degenerative or damaged condition. An effective amount can be determined on an individual basis and will be based, in part, on consideration of the symptoms to be treated and results sought. An effective amount can be determined by one of ordinary skill in the art employing such factors and using no more than routine experimentation.

In preferred methods, an effective amount of the interferon polynucleotide sequence contained within its attendant vector (i.e., "carrier") may be directly administered to a target cell or tumor tissue via direct injection with a needle or via a catheter or other delivery tube placed into the cancer or tumor or blood vessel feeding the tumor. Dosages will depend primarily on factors such as the condition being treated, the selected interferon, the age, weight, and health of the subject, and may thus vary among subjects. If a viral gene therapy vector is employed, an effective amount for a human subject is believed to be in the range of about 0.1 to about 10 ml of saline solution containing from about $1\times10^7$ to about $1\times10^{12}$ plaque forming units (pfu)/ml interferon containing, viral expression vectors.

As discussed above, the IFN gene could be administered by direct injection into solid tumors. Alternatively, delivery into the tumors could be done by infusion into a blood vessel which feeds the tumor. Parenteral administration of the vector is also possible. Polynucleotides encoding interferon may be administered topically, intraocularly, parenterally, intranasally, intratracheally, intrabronchially, intramuscularly, subcutaneously or by any other means. Parenteral administrations will include intravenous, intramuscular, intraperitoneal, and subcutaneous. A more sophisticated approach may be parenteral administration of a virus or chemical conjugate which localizes to a distinct tumor type due to a natural tropism or due to the presence of a surface molecule which binds to a receptor found only on certain tumor types.

As described above, the present invention provides methods for forming a cell expression system for expressing a gene product (e.g., a interferon) in a mammalian recipient, the expression system produced thereby and pharmaceutical compositions containing the same. The following Examples are directed to demonstrating the feasibility of cell gene therapy in an animal model system

EXAMPLE 1

Exemplary Animal Model

In vivo testing of polynucleotides capable of expressing interferon in an animal model is conveniently accomplished. Tumors are formed in nude mice by injecting human tumor cell lines into the mice. The nude mice (strain nu/nu) are immunodeficient and will not reject the foreign tumor cells. Tumors form 1-2 weeks after tumor cell injection, although the exact timing depends upon the number of cells injected and the tumorigenicity of the cell lines. Polynucleotides expressing interferon are introduced into the tumor cells by conventional transfection procedures in culture prior to injection into the mice. Alternately, the appropriate polynucleotide may be introduced into the tumor by transfection or viral transduction in vivo after the tumors have formed in the mice.

As but one example, the cells used are either the bladder carcinoma cell line HTB9 (Huang et al., supra) or the retinoblastoma cell line WERI-Rb27 (both Takahashi et al., *Proc. Nat. Acad. Sci. USA* 88:5257-5261, 1991. For delivery of the isolated polynucleotide encoding interferon in culture, tumor cells are transfected (using a conventional procedure such as calcium phosphate precipitation, electroporation, or lipofectamine transfection) or directly infected (using a retrovirus, adenovirus, baculovirus, or adeno-associated virus). In the case of an efficient viral infection in which 100% of cells have successfully incorporated the appropriate polynucleotide, no selection of cells is required. Furthermore, it has been discovered (Example 3) that only a small percentage of cells need express the interferon gene, so that drug selection usually will not be required.

If selection is performed in the case of transfections which are not as efficient as, the viral infections described herein, cells are transfected with an expression vector encoding both a drug-resistance gene (such as the neo gene which encodes G418 resistance) and a polynucleotide such as the interferon gene. A control transfection is a vector encoding the drug-resistance gene alone.

After about 2-3 weeks of selection in the drug-containing media, the cell colonies are pooled and subcutaneously injected into the flank of nu/nu (nude) female mice at a cell number of about $10^6$ in a volume of about 100 ul. Virus-infected cells are injected directly without the need for a selection step. The mice are further maintained for at least two months and tumor size is monitored on a weekly basis using calipers.

Alternately, untransfected or uninfected tumor cells are subcutaneously injected in the flank of the mice. After tumor formation, DNA or virus containing a polynucleotide encoding an interferon are injected directly into the tumors. Many viruses are suitable for this procedure, although recombinant adenoviruses are the most efficient and recombinant retroviruses have the advantage of being stably integrated into the tumor cell genome. DNA can be introduced into the cells by mixing the DNA with cationic liposomes and injecting the mixture. DNA or viruses not containing the interferon gene are injected into tumors of other mice to serve as the control. Tumor progression or reduction is monitored with calipers.

EXAMPLE 2

Exemplary Lung Carcinoma Model

As a further example, treatment of human small cell lung carcinoma with liposome-encapsulated, isolated polynucleotide encoding interferon may be performed in vivo by introducing a polynucleotide encoding interferon into cells in need of such treatment using liposomes, in particular small-particle liposome aerosols. Administered via aerosols, polynucleotide encoding interferon is deposited uniformly on the surface of the nasopharynx, the tracheobronchial tree and in the pulmonary area. See, Knight and Gilbert, *Eur. J. Clin. Micro.* and *Infect. Dis.*, 7: 721-731 (1988) for discussion of liposome aerosols. To treat lung cancers in this way, the polynucleotide encoding interferon is purified, by any other convenient method. The polynucleotide encoding interferon is mixed with liposomes and incorporated into them at high efficiency. Since the aerosol delivery is mild and well-tolerated by normal volunteers and patients, the polynucleotide encoding interferon-containing liposomes are administered to treat patients suffering from lung cancers of any stage. The liposomes are delivered by nasal inhalation or by an endotracheal tube connected to a nebulizer at a dose sufficient to inhibit tumor growth. Aerosolization treatments are administered daily for two weeks, with repetition as needed.

In vivo studies using orthotopic small cell lung carcinoma may be carried out using tumor injected into the right mainstream bronchus of athymic (nu/nu) nude mice (about $1.5 \times 10^6$ cells per mouse). Three days later, the mice begin a course of treatment (daily for three consecutive days) of being inoculated endobronchially with a liposome-encapsulated interferon gene and controls lacking the interferon gene sequences. Tumor formation and size are followed in both treatments by measurement with calipers and mouse survival is assessed.

EXAMPLE 3

Ex vivo Gene Therapy with Interferon-beta 1a Gene

In this Example, I use the human breast carcinoma cell line MBA-MD468 (obtained from the American Type Culture Collection). Cells are either uninfected or infected with an adenovirus expressing the human interferon-beta1a gene. In this case, the adenovirus is deleted of the E1 genes and has a temperature sensitive mutation in the E2a gene. Methods of generating this particular adenovirus can be found in Engelhardt et al., (1994), Gene Therapy 5: 1217-1229 (see also below for additional details). Briefly, the interferon-beta1a gene was previously cloned into the adenovirus vector pAdCMVlink1 such that gene transcription would be driven by the CMV IE1 promoter, thereby creating an adenovirus transfer plasmid. The gene was inserted into this vector in place of the deleted E1 gene. A recombinant adenovirus having this interferon gene is generated by recombination of the transfer plasmid and the adenovirus genome in 293 cells. Virus is plaque-purified and titered in plaque assays by conventional methods.

Materials and Methods

Cell Culture. Human Carcinoma cells MDA-MB468, Huh7, KM12LA4, ME180, HeLa, U87, and 293 are maintained as adherent cultures in Dulbecco's modified Eagle's. medium containing 10% bovine serum, 2 mM glutamine, penicillin and streptomycin, non-essential amino-acids, and vitamins.

Generation of Purified Adenoviruses. An adenovirus transfer vector encoding the human IFNIβ gene driven by the cytomegalovirus early promoter, pAdCMV-huIFNβ, is constructed by ligating a cDNA insert encoding human IFN-β1a into the plasmid pAdCMVlink1 (see Engelhardt et at, 1994, supra). Plasmid pAdCMV-huIFNβ is co-transferred into 293 cells with genomic DNA purified from the temperature-sensitive adenovirus H5ts 125. Recombinant adenoviruses derived from individual plaques are used to infect 293 cells at 39° C. and the supernatants tested for IFN-β gene expression by an ELISA assay. An adenovirus carrying the IFN-β cDNA (H5.110 hlIFNβ) is identified and further amplified. Similarly, a control E2A temperature-sensitive adenovirus encoding the colorimetric marker β-galactosidase (H5.110lacZ) is made. Virus preparations are produced in 293 cells and purified on CsCl gradients after two rounds of plaque isolation. They were shown to be negative for the presence of wild-type adenovirus.

Subconfluent cells are infected with H5.110hlIFNβ at multiplicity of infection (MOI) of 100 in 3 ml of medium containing 2% bovine serum. Fifteen to eighteen hours later, supernatants are collected and IFN-β concentration quantified by ELISA assay.

ELISA Assay. 96-well plates are coated overnight at 4° C. with an anti-human IFNβ antibody, B02 (Summit Pharmaceuticals Co., Japan). The antibody is used at 10 μg/ml in the coating buffer containing 50 mM Sodium Bicarbonate/carbonate, 0.2 mM $MgCl_2$, and 0.2 mM $CaCl_2$ (pH 9.6). After the plates are blocked with 1% casein in PBS for 1 hour at room temperature, IFN-β samples of IFN-β protein standards (Avonex™, Biogen), diluted in 1% casein and 0.05% Tween-20, are added. The plates are then successively incubated at room temperature for 1 hour with an anti-IFN-β rabbit sera (1:2000 dilution), 1 hour with horseradish peroxidase (HRP)-conjugated donkey anti-rabbit antibody (Jackson Immuno Research, 1:5000 dilution), and the substrate solution (4.2 mM TMB and 0.1 M Sodium acetate-citric acid pH4.9). After the reaction is stopped by 2N $H_2SO_4$, absorbance was measured at 450 nm.

Mouse Experiments. 4 to 6 week old female Balb/c nu/nu mice are obtained from Taconic farms (Boston, Mass.). All mice are maintained in the pathogen-free Biogen animal facility for at least 2 weeks before each experiment. For the ex vivo experiments, infected and uninfected cells are harvested with trypsin/EDTA solution and washed 2 times with PBS. These cells are mixed just prior to injection into mice at the ratios described below. A total of $2\times10^6$ cells in 100 μl of PBS are implanted subcutaneously into the right flank. Tumor size is measured in length and width by using calipers and presented as the average tumor diameter (mm).

For the in vivo direct injection experiments (Example 4), $2\times10^6$ tumor cells in 100 μl PBS are first subcutaneously implanted into nude mice. When tumor size reached 5-6 mm in diameter, 100 μl of PBS containing various doses of recombinant adenoviruses are injected directly into the center of the tumor in a single injection. Tumors are monitored in length and width using calipers. Tumor size is calculated by averaging the length and width. Animal death is defined by sacrificing mice in which tumors began to show signs of bleeding or reached 10% of total body weight.

Apoptosis is examined by using the In Situ Apoptosis Detection Kit provided by Oncor, Inc. (Catalog # S7110-KIT).

Results

I initially evaluated the transduction efficiency and transgene expression of the adenovirus vectors. Human breast carcinoma cells MDA-MB-468 are infected with H5.110lacZ at increasing multiplicities of infection (MOI). After X-gal staining, I estimated that at an MOI of 100, the gene transduction efficiency reached approximately 100% in these cells (data not shown). Thus, the breast carcinoma cells are infected in culture at a ratio of 100 plaque forming units (pfu) per cell since our experience with these carcinoma cells indicated that this was the lowest virus:cell ratio which would lead to expression of the gene in every cell in the population.

For the first experiment, 18 hours after infection, $2\times10^6$ cells are injected subcutaneously into the back of each nude mouse. Five mice are injected with uninfected cells and five mice are injected with cells infected with adenovirus-IFNβ. Tumors of significant size arose in all of the mice injected with the control uninfected cells. No tumors appeared in any of the mice injected with cells treated with adenovirus expressing IFN-β (H5.110hIFNβ: Table 1).

To rule out the possibility that in vitro exposure of tumor cells to IFN-β protein might lead to the loss of tumorigenicity in vivo, I treated MDA-MB-468 cells with IFN-β protein at the protein concentration that was detected after the 18 hour virus infection. After thorough washing, equal number of treated cells, or untreated cells, or the mixture containing 10% treated cells, are injected into the nude mice. Tumor development is observed in all three groups of mice (data not shown), indicating that the ex vivo IFN-β gene delivery, but not in vitro protein treatment, is critical to the inhibition of tumor formation.

To determine if cancer cells expressing the IFN-β gene could lead to the destruction of non-transduced cells, the following experiment is performed. The same cancer cells are either uninfected, infected with adenovirus expressing the IFN-β gene (H5.110hIFNβ) or infected with the same type of adenovirus but expressing the lacZ gene (H5.110lacZ) which encodes the β-galactosidase reporter protein which would not be expected to have any anticancer effect and, therefore, is a control for any effects by the adenovirus itself. All the adenovirus infections are done at a pfu:cell ratio of 100. I separately infected MDA-MB-468 tumor cells with H5.110hIFNβ or H5.110lacZ at an MOI at 100. At 18 hours after infection, the infected cells were harvested and a portion of them were mixed with uninfected cells just prior to injection into mice. Balb/c nude mice were implanted subcutaneously with equal number of infected cells, uninfected cells, or a mixture containing 10% infected cells and 90% cells which were not exposed to the virus. Tumor growth was monitored twelve days later. While all mice implanted with uninfected cells developed tumors, no tumors are observed in mice that received 100% H5.110hIFNβ or H5.110lacZ infected cells, suggesting that infection by either virus can abolish tumorigenicity (Table 1). However, all mice that received 10% H5.110lacZ infected cells developed tumors, while all mice that received 10% H5.110hIFNβ infected cells failed to do so. Therefore, H5.110lacZ infection, although sufficient to suppress the tumor formation of the already-infected cells, failed to block the tumorigenicity of the co-injected naive and uninfected cells. In contrast, transduction by H5.110hIFNβ in 10% of cells was enough to suppress the tumorigenicity of the cells which had been transduced by the virus as well as those which had not been transduced. Inhibition of tumor formation by H5.110lacZ in the 100% transduced population could be due to some general toxic effects or to some anti-tumor effects of this generation of adenovirus, but it should be noted that transduced cells were capable of replication in vitro (unpublished data).

To establish the amount of interferon-containing virus needed to suppress tumorigenicity, the H5.110hIFNβ and H5.110lacZ infected tumor cells separately are mixed with uninfected cells at various ratios such that there was an excess of uninfected cells in each instance. The mixings are such that different samples consisted of 10%, 3%, 1%, 0.3% cells infected with the adenovirus and the remainder uninfected. Immediately after mixing, the cells are injected into the nude mice. The results are shown in Table 1. The tumor diameters are measured in two dimensions at various times after injection of the cells. Each data point in Table 1 represents the average +/− standard deviation of the lateral and longitudinal diameter measurements from four mice. Measurements are taken at 12, 19, 26 and 33 days after injection of the tumor cells.

TABLE 1

| Sample | average tumor diameter (in mm) | | | |
| --- | --- | --- | --- | --- |
|  | Day 12 | Day 19 | Day 26 | Day 33 |
| 100% uninfected | 4.1 +/− 0.6 | 4.9 +/− 0.8 | 5.9 +/− 0.5 | 6.3 +/− 0.6 |
| 100% AdV-IFN | 0.0 | 0.0 | 0.0 | 0.0 |
| 10% AdV-IFN | 0.0 | 0.0 | 0.0 | 0.0 |
| 3% AdV-IFN | 0.0 | 0.0 | 0.0 | 0.0 |
| 1% AdV-IFN | 0.0 | 0.0 | 0.0 | 0.0 |
| 0.3% AdV-IFN | 2.8 +/− 0.2 | 2.9 +/− 0.3 | 3.0 +/− 0.6 | 1.8 +/− 2.0 |
| 100% AdV-lacZ | 0.0 | 0.0 | 0.0 | 0.0 |
| 10% AdV-lacZ | 4.8 +/− 0.4 | 5.2 +/− 0.6 | 6.2 +/− 0.5 | 6.5 +/− 0.5 |
| 3% AdV-lacZ | 4.3 +/− 0.5 | 4.6 +/− 0.6 | 5.8 +/− 0.8 | 6.5 +/− 1.0 |
| 1% AdV-lacZ | 4.3 +/− 0.4 | 4.6 +/− 0.4 | 5.0 +/− 0.5 | 6.3 +/− 0.9 |
| 0.3% AdV-lacZ | 4.4 +/− 0.5 | 4.7 +/− 0.6 | ND | ND |

Tumor development was completely blocked in mice that received as few as 1% H5.110hIFNβ transduced cells (Table 1). In the first week after injection of the cells, very small tumors could be detected (these are palpable, but not big enough to be measured) in the mice injected with the 10, 3 and 1% H5.110hIFNβ However, all of these small tumors completely regressed by day 9. This suggests that some cells survived for a short time and expressed the IFN-β gene during this period, leading to death of the entire tumor. In the several experiments performed with this cell line in nude mice, tumor formation has never been observed when 1% of cells were transduced with H5.110hIFNβ and survival has been 100% (data not shown). Mice that received 0.3% H5.110hIFNβ transduced cells developed tumors, however, the size of these tumors was significantly smaller than those in the control mice and 2 out of 5 mice in this 0.3% group had complete regression by day 33 (Table 1).

In contrast, mice that receive 10% to 0.3% H5.110lacZ treated cells develop tumors with similar sizes as the uninfected group and no tumor regression was observed in either of these control groups (Table 1).

Figure 1B:
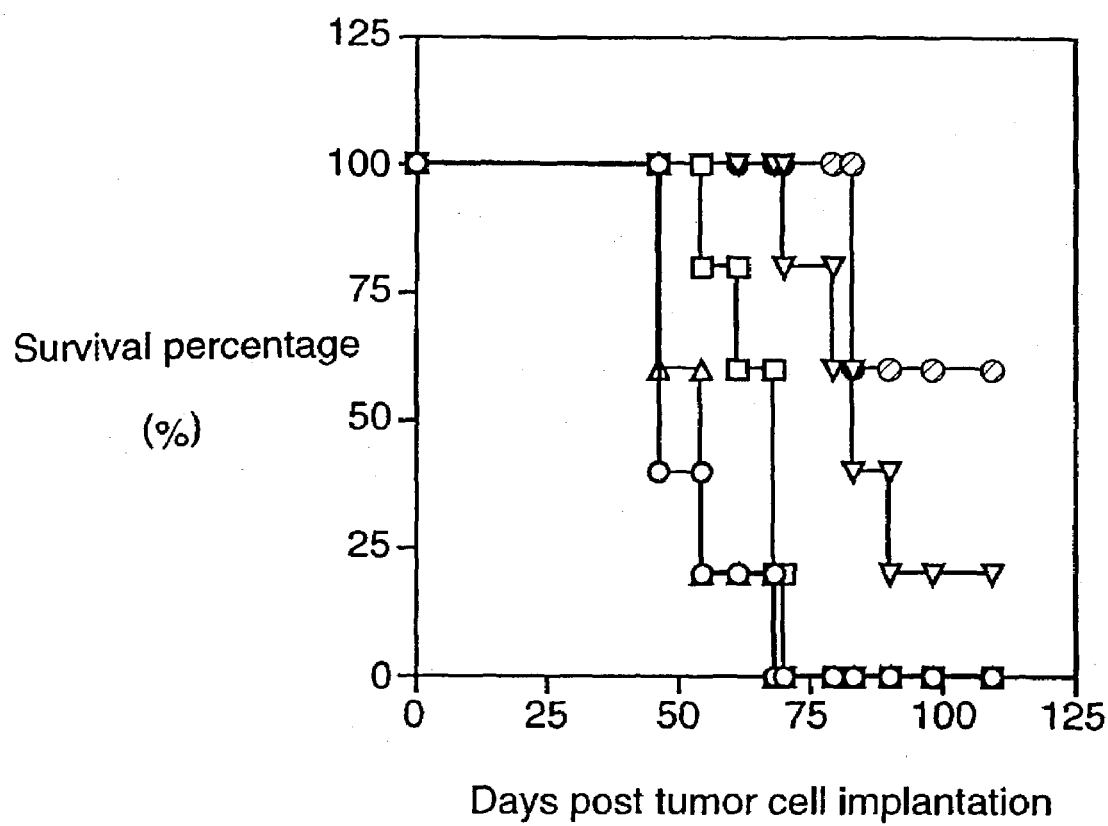

Clearly, expression of human interferon beta (hIFN-β) in only a very small percentage cells appeared to block tumorigenesis in nude mice. I further examined the lowest ratio for H5.110hIIFNβ infected cells required to affect, but not necessarily block, tumor formation and promote mouse survival. Equal numbers of MDA-MB-468 cells containing 0.3%, 0.1%, 0.03%, 0.01%, and 0% H5.110hIFNβ infected cells are implanted into nude mice and tumor growth was monitored. Mice that receive 0.3% or 0.1% infected cells develop much smaller tumors compared with those that received only uninfected cells (FIG. 1A). Of the tumors which formed at 0.3 and 0.1% transduction, 3 out of 5 and 1 out of 5 tumors, respectively, regressed completely. Significantly prolonged survival was observed in the 0.3% and 0.1% transduction groups. While implantation of 0%, 0.01%, or 0.03% infected cells resulted in the death of all animals within 75 days, 1 out of 5 and 3 out of 5 animals were alive without tumors in the 0.1% and 0.3% groups, respectively, at the conclusion of this experiment on day 109 (FIG. 1B).

It is likely that only a small portion (greater than about 0.3%, preferably greater than about 1.0% ) of all the tumor cells will need to be transfected or infected in order to have efficacy. This differs from such anticancer gene therapy approaches such as delivery of wild type tumor suppressors (p53, for example) in which every cell in the tumor will need to obtain the tumor suppressor gene.

Thus, the interferon gene demonstrates a potent antiproliferative effect in vivo after in vitro infection. Controls indicate that this was due to interferon rather than the adenovirus.

Ex vivo IFN-β Gene Therapy in Other Human Xenograft Tumors

Figures 1, 2A:
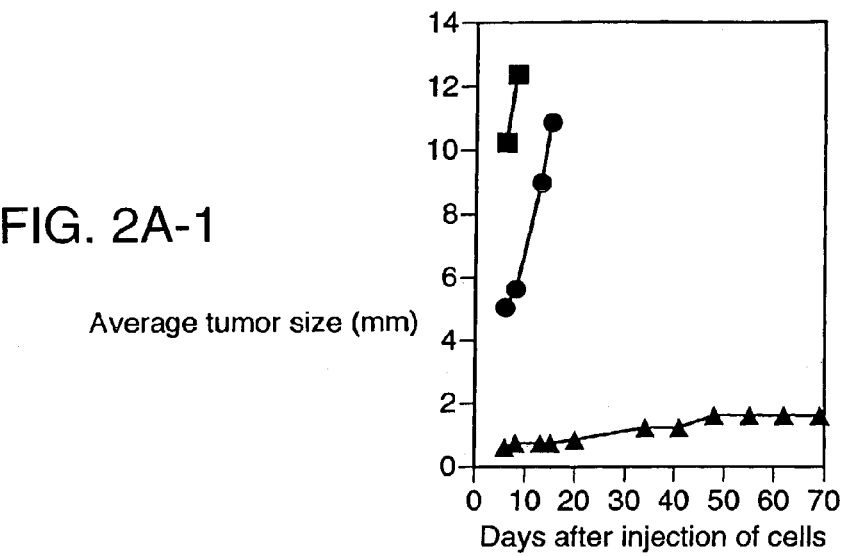
Figures 2, 2A:
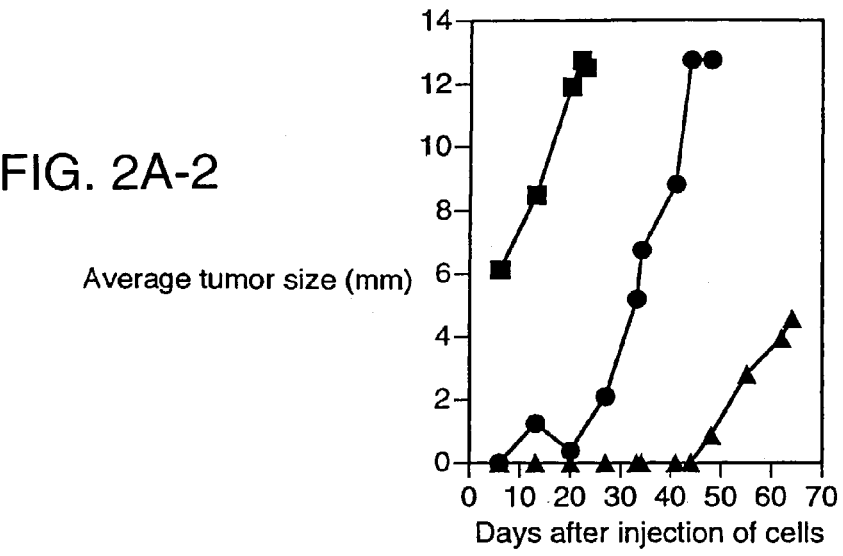
FIG. 2. (A) Ex vivo interferon beta gene therapy in: (1) KM12L4A cells; (2) Huh7 cells; and (3) ME180 cells. Mean tumor size was plotted versus time following tumor cell implantation. Mice were implanted with uninfected cells (-■-), or H5.110hIFNβ infected cells at 1% (-●-), or 10% (-▲-). In those groups in which some mice were sacrificed, the tumor size is presented as the average with the last value carried forward for the sacrificed animals. Discontinuation of the plots reflects the death or sacrifice of all animals in a group. (B) Percentage survival of mice over the observation period of 70 days. Panels 1, 2, and 3 show the data generated with mice implanted with KM12L4A cells, Huh7 cells, and ME180 cells respectively. The symbols represent mice that were implanted with uninfected cells (-■-), H5.110hIFNβ infected cells at 1% (-●-) or 10% (-▲-).

I also tested the effect of H5.110hIFNβ transduction in other tumor cell types in the ex vivo human xenograft model. Human colon carcinoma cells KM12L4A, human liver carcinoma cells Huh7, or human cervical carcinoma cells ME180 are transduced with H5.110hIFNβ Equal number of cells containing 10%, 1%, or 0% transduced cells are tested for their ability to form tumors in nude mice. Injection of uninfected cells of the three types causes the formation of fast growing tumors in all mice. In contrast, ex vivo delivery of 10% H5.110hIFNβ infected cells leads to either no tumor development or the delayed appearance of slower growing tumors in all animals examined (FIG. 2A). Unlike results obtained with MDA-MB-468 cells in which 1% transduction by H5.110hIFNβ completely prevented tumor formation, 1% transduction of these three cell types results in the formation of tumors, although their sizes are smaller than the uninfected controls at each time point. Mice that received 10% and 1% transduced cells exhibit prolonged survival compared to those that received uninfected cells (FIG. 2B). Thus, ex vivo adenovirus-mediated IFN-β gene delivery into multiple different tumor cells results in efficient inhibition of tumorgenicity and leads to increased animal survival time.

EXAMPLE 4

In vivo Gene Therapy with Interferon-beta 1a Gene

Instead of an ex vivo approach direct in vivo gene therapy can be performed. In in vivo gene therapy, the gene is directly administered into the patient. In this Example, adenovirus having the human IFN-β gene (H5.110hIFNβ is directly injected into solid tumors. Briefly, $2 \times 10^6$ MBA-MD-468 human breast carcinoma cells are injected subcutaneously into the back of fifty nude mice. Subcutaneous tumors of approximately 5-6 mm diameter form in nude mice 24 days following subcutaneous injection of MDA-MB-468 ceus. At this time, tumors were treated with PBS or the H5.110hIFNβ and H5.110lacZ vectors at various viral doses ranging from $1\times10^7$ to $3\times10^9$ pfu/mouse in a single intratumor injection.

Figures 2, 2A, 3:
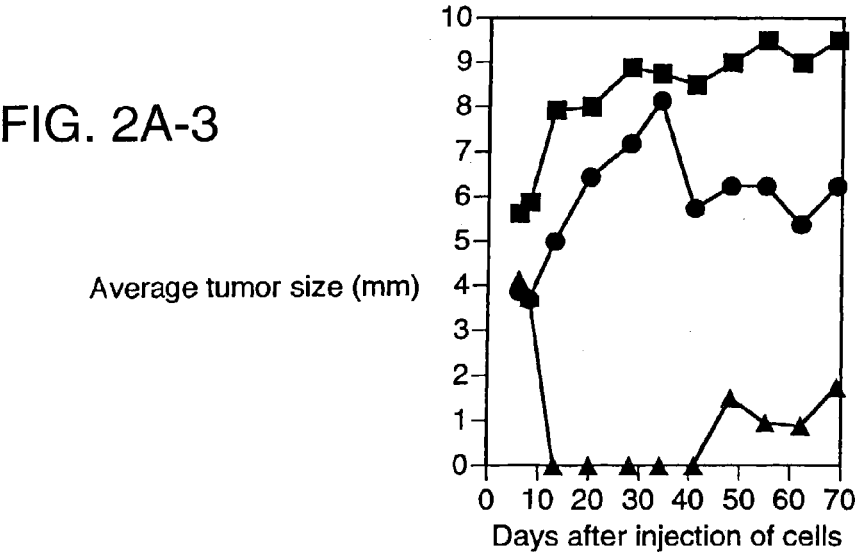
FIG. 3. Direct in vivo treatment of established MDA-MB-468 tumors. Tumors were injected with H5.110hIFNβ at $3\times10^9$ pfu (---), $1\times10^9$ pfu (-☐-), $3\times10^8$ pfu (-○-), $1\times10^8$ pfu (-Δ-), and $3\times10^7$ pfu (-∇-) respectively, or with PBS (-⊠-), or with H5.110lacZ at $3\times10^9$ pfu (-◇-), $1\times10^9$ pfu (-▲-), $3\times10^8$ pfu (-×-), and $1\times10^8$ pfu (-▷-) respectively. Tumor sizes were measured over a period of 14 days following the treatment injections.
Figures 1, 2B:
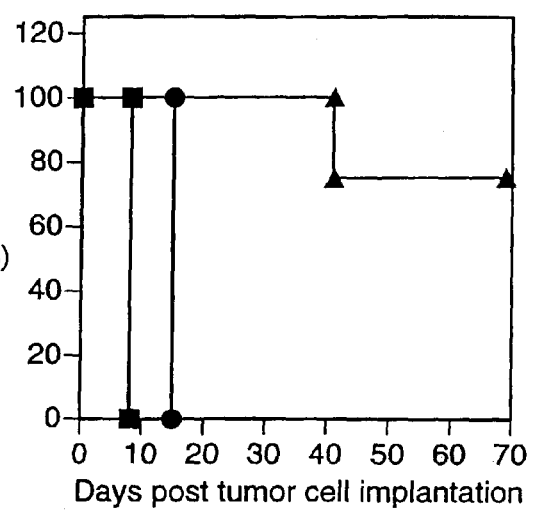
Figures 2, 2B:
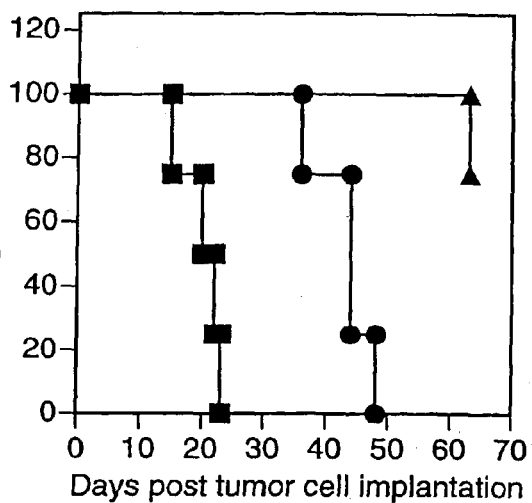
Figures 2, 2B, 3:
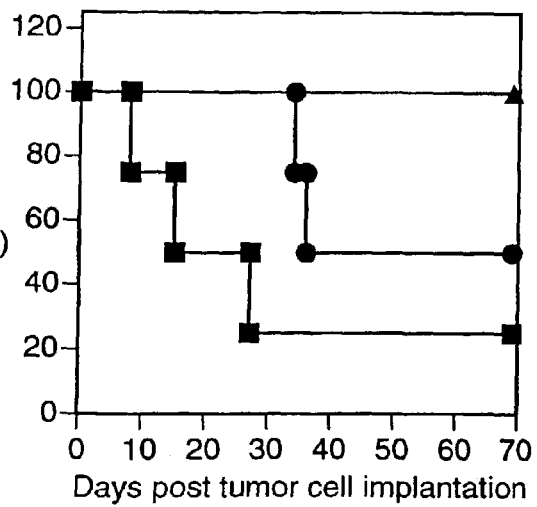
Figure 3:
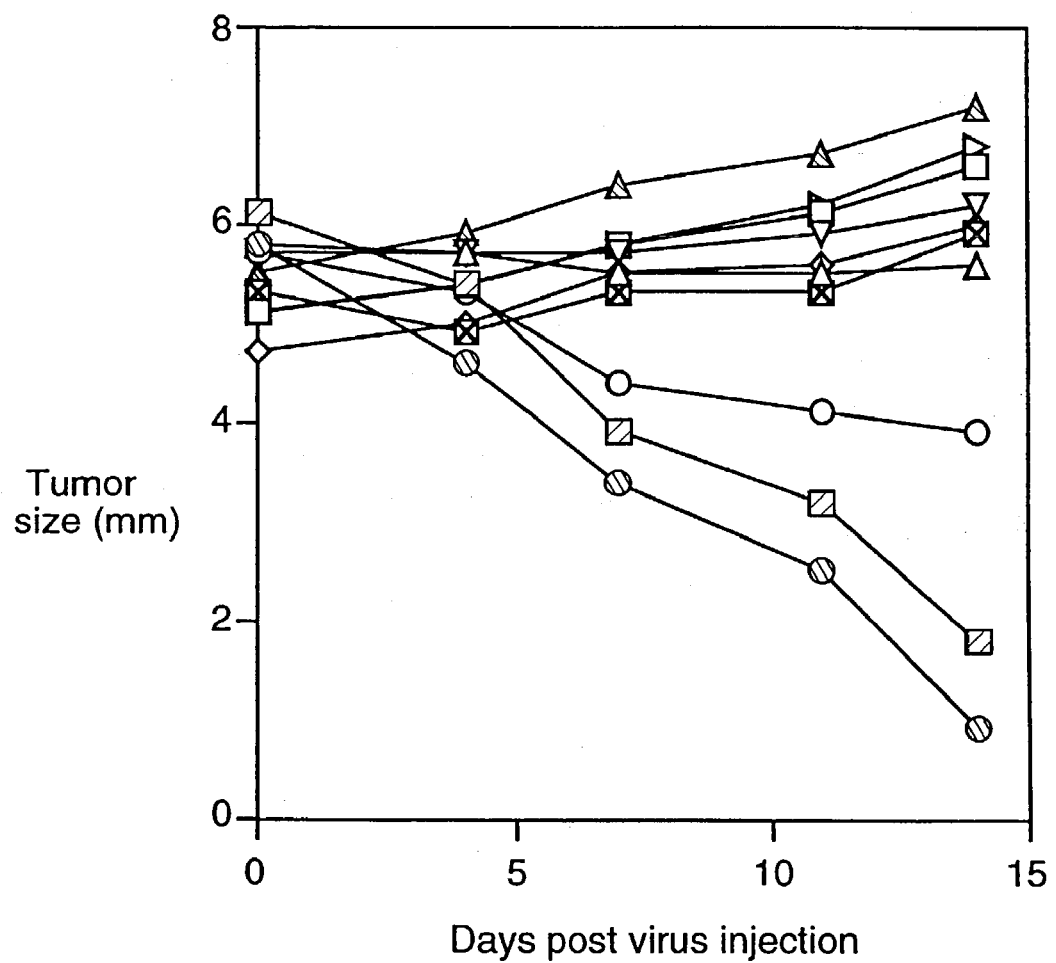

Data shown in FIG. 3 indicate that within 14 days, single dose treatment with H5.110hIFNβ at $3\times10^9$, $1\times10^9$, or $3\times10^8$ total pfu causes tumor regression. Complete tumor regression occurs in 4 out of 5 mice in the $3\times10^9$ pfu group and in 3 out of 5 animals in the $1\times10^9$ pfu treaunent group. In tumors injected with $1\times10^9$ pfu H5.110hIFNβ a high local IFN-β concentration of approximately 1500 IU/ml can be detected while only 37 IU/ml of INF-β is detected in the seruml Lower H5.110hIFNβ doses including $1\times10^8$, $3\times10^7$ and $1\times10^7$ pfu have little or no effect (FIG. 3 and data not shown), indicating that the anti-tumor response is dose-dependent. Injection of PBS or H5.110lacZ at equivalent doses does not lead to tumor regression (FIG. 3.) When the tumors are monitored over a longer period of time, slow growth and regression are observed in some individual tumors injected with H5.110lacZ at $3\times10^9$ pfu, suggesting that the control virus at that dose may cause slight inhibition of tumor growth. Treatment with H5.110hIFNβ at $3\times10^9$, $1\times10^9$, or $3\times10^8$ pfu significantly increases survival relative to PBS or H5.110lacZ treated mice (data not shown). We have also tested multiple injections, with 5 injections of $1\times10^8$ pfu H5.110hIFNβ given every third day into established MDA-MB-468 and HeLa tumors resulting in slower growth and regression of both tumor types (unpublished). I also performed a similar in vivo experiment using the human glioma cell line U87. These cells were very sensitive to IFN-β as complete tumor regression was seen in 4 out of 4 mice treated with $1\times10^9$ pfu H5.110hIFNβ and 2 out of 4 mice treated with $1\times10^8$ pfu (data not shown). These findings demonstrate that direct and local in vivo adenovirus delivery of the IFN-β gene can exert a significant anti-tumor effect.

Four days after injection with $1\times10^9$ pfu virus, the MDA-MB-468 tumors are harvested for histological examination. At that time, tumors injected with H5.110hIFNβ show signs of regression. Histological analysis of the MIDA-MB-468 tumors by hematoxylin-eosin staining is performed. More apoptotic cells are noted in the H5.110hIFNβ-injected tumor than in the H5.1101acZ-injected tumor. I confirmed apoptosis by direct fluorescence detection of end-labeled, fragmented genomic DNA. Very few infiltrating mononuclear cells are observed in the H5.110hIFNβ or HS.1101acZ injected tumors, indicating that the cellular immune response may not play a major role in the H5.110hIFNβ directed tumor regression in this model.

Both the ex vivo and in vivo experiments shown above measure only the direct anti-proliferative effect of interferon. Since these are imrnmune-deficient mice, any immuno-stimulatory activity that interferon has which might stimulate tumor destruction will not be present. Also, since interferons do not cross species from human to mouse, the human IFN-β used to inhibit the human cancer cells in these mice would not be expected to inhibit angiogenesis since the human IFN-β does not act on the mouse vascular endothelial cells. Therefore, it is possible that an even more dramatic anti-cancer activity would be seen when human patients are treated with the adenovirus having the human IFN-β. This could be modeled in immune-competent non-human primates. Alternatively, one could use adenovirus having the murine IFN-β gene in immune-competent mice having tumors of murine origins. Many of these syngeneic mouse tumor models are available.

The data provided here demonstrate a remarkable ability of IFN-β gene therapy to block the formation of tumors de novo as well as to cause regression of established tumors. The ex vivo transdpctions experiments confirmed that introduction of a potent secreted protein into as few as 0.3%-1.0% transduced cells blocked the establishment of MDA-MB-468 tumors. A variety of other tumor cell lines have been tested, and while there was a variation in the potency of the IFN-β effect, all could be blocked with 1-10% of IFN-β transduced cells. Encouraged by the relatively small percentage of IFN-β secreting cells required to impact tumor formation, I then challenged pre-formed tumors with direct intratumor injection of the adenoviruses. Again the effect of the IFN-β gene delivery was potent with single injections of virus resulting in either partial or in some cases complete regression of tumors.

In these studies, the dramatic regression of tumors appeared to be primarily the result of the direct anti-proliferative or cytotoxic activity of IFN-β. This conclusion is supported by the fact that the IFN-β gene used in this study is of human origin, and human IFN-β does not cross react appreciably with the host mouse cells. Also, the immune-deficient nude mice that were used lack T lymphocytes, a major effector cell in the type 1 IFN induced immunostimulation (Tough, D. F. et al., (1996), Science 272: 1947-1950 and Rogge, L. et al., (1997) J. Exp. Med., 185: 825-831). Furthermore, in the rapidly regressing tumors following IFN-β gene delivery, no overt increase in the infiltration of mononuclear cells was observed. These findings support the notion that IFN-β mediated anti-proliferative activity alone could be sufficient to cause tumor regression. Our data appear to be consistent with the clinical correlation previously observed between the in vitro sensitivity of malignant cells to IFN-induced anti-proliferative activity and the in vivo therapeutic effect (Einhorn and Grander (1996) J. Interferon Cytokine Res. 16: 275-281)

In summary, it has been found that adenovirus-mediated IFN-β gene therapy can exert an efficient anti-tumor effect in mouse models. Ex vivo delivery of the IFN-β gene into a very small percentage of cells was sufficient to block tumor formation and single-dose direct intra-tumor IFN-β gene delivery led to regression of established tumors. Without wishing to be bound by any theory of actions, this potent anti-tumor effect, may result from autocrine and paracrine effect of IFN-β. This anti-tumor effect could be a critical factor in gene therapy cancer trials in which the degree of gene delivery is likely to be limiting and a significant bystander effect will be required. Therefore, local IFN-β gene therapy provides a promising strategy for the treatment of tumors in humans.

Equivalents

It should be understood that the preceding is merely a detailed description of certain preferred embodiments. It therefore should be apparent to those skilled in the art that various modifications and equivalents can be made without departing from the spirit or scope of the invention.

What is claimed is:

1. A method for treating cancer by in vivo interferon-β gene therapy comprising the steps of:
   parenterally administering to a subject a viral vector comprising a gene that encodes interferon-β protein, and
   allowing said interferon-β protein to be expressed from said gene in said subject in an amount sufficient to cause cancer regression or inhibition of cancer growth,
   wherein said viral vector is selected from the group consisting of an adenoviral vector, a lentiviral vector, a baculoviral vector, an Epstein Barr viral vector, a papovaviral vector, a vaccinia viral vector, and a herpes simplex viral vector, and wherein if said viral vector is an adenoviral vector, then said subject is not exposed to a nucleic acid encoding a selectable marker gene.

2. The method according to claim 1, wherein said viral vector is selected from the group consisting of an adenoviral vector, a baculoviral vector and a lentiviral vector.

3. The method according to claim 1, wherein said viral vector is an adenoviral vector.

4. The method according to claim 3, wherein said adenoviral vector has a deletion in its E3 gene.

5. The method according to claim 3, wherein said adenoviral vector has a deletion in its E1 gene.

6. The method according to claim 4, wherein said adenoviral vector has a deletion in its E1 gene.

7. The method according to claim 1, wherein said parenteral administration is selected from the group consisting of intravenous administration, intramuscular administration, subcutaneous administration and intraperitoneal administration.

8. The method according to claim 1, wherein said cancer is selected from the group consisting of malignant glioma, melanoma, hemangioma, leukemia, lymphoma, myeloma, colorectal cancer, non-small cell carcinoma, breast cancer and ovarian cancer.

9. The method according to claim 8, wherein said cancer is malignant glioma.

10. The method according to claim 1, wherein said gene encodes a human interferon-β protein.

11. The method according to claim 1, wherein said subject is a human subject.

12. A method for treating cancer by in vivo interferon-β gene therapy comprising the steps of:

parenterally administering to a subject a replication-defective viral vector comprising a gene that encodes interferon-β protein, and allowing said interferon-β protein to be expressed from said gene in said subject in an amount sufficient to cause cancer regression or inhibition of cancer growth, wherein said viral vector is selected from the group consisting of an adenoviral vector, a lentiviral vector, a baculoviral vector, an Epstein Barr viral vector, a papovaviral vector, a vaccinia viral vector and a herpes simplex viral vector, and wherein if said viral vector is an adenoviral vector, then said subject is not exposed to a nucleic acid encoding a selectable marker gene.

13. The method according to claim 12, wherein said viral vector is selected from the group consisting of an adenoviral vector, a baculoviral vector and a lentiviral vector.

14. The method according to claim 12, wherein said viral vector is an adenoviral vector.

15. The method according to claim 14, wherein said adenoviral vector is deficient is one or more essential genes of one or more adenoviral genome regions selected from the group consisting of the E1, E2A and E4 regions of the adenoviral genome.

16. The method according to claim 14, wherein said adenoviral vector has a deletion in its E3 gene.

17. The method according to claim 14, wherein said adenoviral vector has a deletion in its E1 gene.

18. The method according to claim 17, wherein said adenoviral vector is deficient in its E3 gene.

19. The method according to claim 12, wherein said parenteral administration is selected from the group consisting of intravenous administration, intramuscular administration, subcutaneous administration and intraperitoneal administration.

20. The method according to claim 12, wherein said cancer is selected from the group consisting of malignant glioma, melanoma, hemangioma, leukemia, lymphoma, myeloma, colorectal cancer, non-small cell carcinoma, breast cancer and ovarian cancer.

21. The method according to claim 20, wherein said cancer is malignant glioma.

22. The method according to claim 12, wherein said gene encodes a human interferon-β protein.

23. The method according to claim 12, wherein said subject is a human subject.

24. A method for treating cancer by in vivo interferon-β gene therapy comprising the steps of:

administering to a subject a viral vector comprising a gene that encodes interferon-β protein, and allowing said interferon-β protein to be expressed from said gene in said subject in an amount sufficient to cause cancer regression or inhibition of cancer growth by induction of a systemic anti-tumor immune response, wherein said viral vector is selected from the group consisting of an adenoviral vector, a lentiviral vector, a baculoviral vector, an Epstein Barr viral vector, a papovaviral vector, a vaccinia viral vector and a herpes simplex viral vector, and wherein if said viral vector is an adenoviral vector, then said subject is not exposed to a nucleic acid encoding a selectable marker gene.

25. The method according to claim 24, wherein said viral vector is selected from the group consisting of an adenoviral vector, a baculoviral vector and a lentiviral vector.

26. The method according to claim 24, wherein said viral vector is an adenoviral vector.

27. The method according to claim 26, wherein said adenoviral vector has a deletion in its E3 gene.

28. The method according to claim 26, wherein said adenoviral vector has a deletion in its E1 gene.

29. The method according to claim 27, wherein said adenoviral vector has a deletion in its E1 gene.

30. The method according to claim 24, wherein said gene encodes a human interferon-β protein.

31. The method according to claim 24, wherein said subject is a human subject.

* * * * *